US006673988B1

(12) United States Patent
Cahoon

(10) Patent No.: US 6,673,988 B1
(45) Date of Patent: Jan. 6, 2004

(54) PLANT LIPASES

(75) Inventor: Edgar B. Cahoon, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 122 days.

(21) Appl. No.: 09/668,097

(22) Filed: Sep. 22, 2000

Related U.S. Application Data
(60) Provisional application No. 60/157,309, filed on Oct. 1, 1999.

(51) Int. Cl.[7] .......................... A01H 5/00; C12N 15/82; C12N 5/04; C07H 21/04
(52) U.S. Cl. ...................... 800/298; 800/281; 435/419; 435/468; 435/471; 435/252.3; 536/23.2; 536/23.6
(58) Field of Search ............................... 536/23.2, 23.6; 435/69.1, 419, 468, 471, 252.3; 800/281, 298

(56) References Cited

PUBLICATIONS

Chris Upton et al, TIBS20—May 1995, pp. 178–179 "A New Family of Lipolytic Enzymes?".
Bork et al, Trends in Genetics, vol. 12, No. 10: 425–427, Oct. 1996.*
Brenner, S.E., Trends in Genetics, Vol 15, No. 4: 132–133, Apr. 1999.*
Smith et al, Nature Biotechnology, vol. 15: 1222–1223, Nov. 1997.*
Doerks et al, Trends in Genetics, vol. 14, No. 6: 248–250, Jun. 1998.*
Van de Loo et al, Proc. Natl, Acad. Sci, USA, vol. 92: 6743–6747, Jul. 1995.*
Broun et al, Science, vol. 282: 131–133, Nov. 13, 1998.*
DeLuca, V., AgBiotech News and information, vol. 5, No. 6: 225N–229N, 1993.*
David J. Brick et al., FEBS Letters, vol. 377:475–480, 1995, A New Family of Lipolytic Plant Enzymes with Members in Rice, Arabidopis and Maize.
National Center for Biotechnology Information General Identifier No. 569288, Nov. 11, 1994.
National Center for Biotechnology Information General Identifier No. 570021, Nov. 11, 1994.
National Center for Biotechnology Information General Identifier No. 702247, Mar. 9, 1995.
National Center for Biotechnology Information General Identifier No. 3763803, Oct. 19, 1998.
National Center for Biotechnology Information General Identifier No. 3763804, Oct. 19, 1998.
National Center for Biotechnology Information General Identifier No. 3768136, Oct. 20, 1998.
National Center for Biotechnology Information General Identifier No. 4715132, Apr. 29, 1999.
National Center for Biotechnology Information General Identifier No. 4716417, Apr. 29, 1999.
National Center for Biotechnology Information General Identifier No. 4827484, May 14, 1999.
National Center for Biotechnology Information General Identifier No. 5455457, Jul. 13, 1999.
National Center for Biotechnology Information General Identifier No. 5455577, Jul. 13, 1999.
National Center for Biotechnology Information General Identifier No. 545582, Jul. 13, 1999.
National Center for Biotechnology Information General Identifier No. 5455586, Jul. 13, 1999.
National Center for Biotechnology Information General Identifier No. 4314378, Mar. 2, 1999.
National Center for Biotechnology Information General Identifier No. 2129636, Jul. 21, 2000.
National Center for Biotechnology Information General Identifier No. 4678342, Apr. 19, 2000.
National Center for Biotechnology Information General Identifier No. 5734636, Dec. 3, 1999.
National Center for Biotechnology Information General Identifier No. 5734634, Dec. 3, 1999.
National Center for Biotechnology Information General Identifier No. 3776573, Oct. 21, 1998.
National Center for Biotechnology Information General Identifier No. 2191137, Jun. 12, 1997.
National Center for Biotechnology Information General Identifier No. 4314378, Mar. 2, 1999.
National Center for Biotechnology Information General Identifier No. 5306262, Apr. 5, 2000.
Xiaoying Lin et al., Nature, vol. 402:761–768, 1999, Sequence and analysis of Chromosome 2 of the Plant Arabidopsis Thaliana.
National Center for Biotechnology Information General Identifier No. 4678342, Apr. 19, 2000.
National Center for Biotechnology Information General Identifier No. 6691210, Jun. 28, 2000.
National Center for Biotechnology Information General Identifier No. 7523500, Jun. 28, 2000.
National Center for Biotechnology Information General Identifier No. 7523511, Jul. 28, 2000.

* cited by examiner

*Primary Examiner*—Elizabeth F. McElwain

(57) ABSTRACT

This invention relates to an isolated nucleic acid fragment encoding a lipase. The invention also relates to the construction of a chimeric gene encoding all or a portion of the lipase, in sense or antisense orientation, wherein expression of the chimeric gene results in production of altered levels of the lipase in a transformed host cell.

11 Claims, 7 Drawing Sheets

Figure 1 (page 1 of 7)

```
                                                          *** *  *   *
SEQ ID NO:39    MA-----SQDCHML--LSFFISTFLITVV--TSQTRC-------RNFKSIISFGD S ITDTG
SEQ ID NO:40    MA-----SSLKKLI--SSFLLVLYSTTIIVASSESRC-------RRFKSIISFGD S IADTG
SEQ ID NO:41    M---SSSISPL-------LTTAISVAILLFSTISTAATIPNIHRPFNKIYAFGD S FTDTG
SEQ ID NO:2     MAVL----------WGCLFIVVGFPFGCN---CEVLKKCK---FDAIYQFGD S LADTG
SEQ ID NO:4     MG----------G-RGAMLAVLVVLAAV--GAAAESMEAAAKGRYHALFNFGD S LADAG
SEQ ID NO:8     MG----------AVRGILVVAVVLAVAAILAGAAEGKVNGKAKGKYRALFNFGD S LADAG
SEQ ID NO:10    MM----------GRQSSSAARRV-VVVVCAAMV----VAAAAAQKYNAVYNFGD S ITDTG
SEQ ID NO:14    MKI----------SILFITI-----FSCGFLGNVVSNASPLPYEAIFNFGD S ISDTG
SEQ ID NO:16    MPLSAKISSLQRQIQRLRIVLVLLL---LLAATVTAC------YTSLFSFGD S LTDTG
SEQ ID NO:22    MG----------G-RGAMLAVVLVVLAAV--GAAAESMEAAAKGRYHALFNFGD S LADAG
SEQ ID NO:26    M--ASCVSSMSSTI--LILIAICTLSSLL--SAASAATEEGRTRPFKRVYAFGD S FTDTG
SEQ ID NO:28    MG-----STISLALLVF--AVLLLNADLGSCGC-------FKRIFAFGD S IIDTG
SEQ ID NO:30    ME--------H-RGLLL----VLVAAACLSGGAHAR----HAKKSYGAVFSFGD S LSDAG
SEQ ID NO:32    TS----------ILFLLSVS-----LCGTSWQSYDAIYNFGD S ISDTG
SEQ ID NO:34    MAVS---------RLSVLVAALACCCL---ARLAQCGGGGGQNYTSMFSFGD S LTDTG
SEQ ID NO:36    MA----------SSP-------LLVALVMVSAC------FLAVSGQKFNAIYSFGD S MSDTG
SEQ ID NO:38    MA----------RPSSSPMATRLPLLLVLLSSL----ALQAAAQKYNAVYSFGD S ITDTG
                1                                                          60
```

Figure 1 (page 2 of 7)

```
                   *           ***              *             *             *              *
SEQ ID NO:39   NLLGLSSPNDLPESAFPPYGETFFHHPSGRFSDGRLIIDFIAEFLGIPHVPPFYGSKNG-
SEQ ID NO:40   NYLHLSDVNHLPQSAFLPYGESFFHPPSGRASNGRLIIDFIAEFLGLPYVPPYFGSQNV-
SEQ ID NO:41   NSRSGEGPAGFGHLSSPPYGMTFFRRPTNRYSDGRLTIDFVAESMNLPFLPPYLSLKTTN
SEQ ID NO:2    NLIRENPQTPF---SRLPYGQTFFNRPTGRCSNGLLMLDYFSLAAGLPLANPYLK--KNA
SEQ ID NO:4    NLIQNGTPEILA-TARLPYGQTYFGRATGRCSDGRLVIDHLAQEFGLPLLPP-----SK--
SEQ ID NO:8    NLLANGVDFRLA-TAQLPYGQTFPGHPTGRCSDGRLVVDHLADEFGLPLLPP-----SK--
SEQ ID NO:10   NLCTNGRPSQIT-FTQPPYGETYFGSPTCRCCDGRVVVDFLASKFGLPFLPP-----SKST
SEQ ID NO:14   NAAHNHPPMP-----GNSPYGSTYFKHPSGRMSNGRLIIDFIAEAYGMPMLPAYLNLTKGQ
SEQ ID NO:16   NLY-FISPRQSPDCLLPYGQTHFHRPNGRCSDGRLILDFLAESLGLPYVKPYLGFKNGA
SEQ ID NO:22   NLIQNGTPEILA-TARLPYGQTYFEGKPTGRCSDGRLVIDHLAQEFGLPLLPP-----SK--
SEQ ID NO:26   NTKNAEGPSGFGHVSNSPYGTTFFNHSTNRYSDGRLVIDFVAEALSLPYLPPY-------
SEQ ID NO:28   NFHPGS-------MWSPPYGGTYFEHRPTGRCSDGRLIVDFYAQALGLPLLPP-----SGPE
SEQ ID NO:30   NLIVDGIPKSLT-TARSPYGMTFFEGRPTGRCSNGRVVVDELAEHFGLPLPPA-----SQ--
SEQ ID NO:32   NLCTGGCPSWLT-MGQPPYGTSYFEGRPTGRCSDGRVVVDFLAQFFRLPLLPP-----SKSK
SEQ ID NO:34   NLL--VSSPLSFNIVGREFPYGMTYFEHRPTGRCSDGRLVVDFLAQAFGLPLLQPYLS----
SEQ ID NO:36   NLCVNGPPAGLT-LTQPPYGETFFGRATCRCSDGRLVVDFLAEKFGLPLLKP-----SKQG
SEQ ID NO:38   NLCTNGRPSAIT-FTQPPYGETYFGSPTCRCSDGRVIVDFLSTKYGLPFLPP-----SKST
                61                                                              120
```

Figure 1 (page 3 of 7)

```
                    *   *  *        *                                                                                                180
SEQ ID NO:39        ----NFEK-GVNFAVGGATALECSVLEEK-GTHCSQ-SNISLGNQLKSFKESLPYLCGSS
SEQ ID NO:40        ----SFEQ-GINFAVYGATALDRAFLLGK-GIESDF-TNVSLSVQLDTFKQILPNLCASS
SEQ ID NO:41        ANGTATDTHGVNFAVSGSTVIKHAFFVKN-NLSLDM-TPQSIETELAWFEKYLETL-GTN
SEQ ID NO:2         ----SFTH-GVNFAVAGSTALSFRDLAQM-NISSPV-TNSSLGKQLDWMHTHLNTIC-CN
SEQ ID NO:4         ATNASFAY-GANFAITGATALDTPYFEAK-GLGAVIWNSGALMTQIQWFRDLKPFFCNTT
SEQ ID NO:8         LKNSSFAH-GANFAITGATALDTPYFEAK-GLGAVVWNSGALLTQIQWFRDLKPFFCNST
SEQ ID NO:10        --SADFKK-GANMAITGATAMDANFFRSL-GLSDKIWNNGPISFQIQWFQQISSSVC-GQ
SEQ ID NO:14        ---DIKK-GVNFAYAGSTALDKDFLVQK-RINIEE-ATFSLSAQFDWFKGLKSSLC-TS
SEQ ID NO:16        VKRGNIEQ-GVNFEAVAGATALDRGFFEEK-GFAVDVTANFSLGVQLDWFKELLPSLCNSS
SEQ ID NO:22        AKNASFAH-GANFAITGATALDTPYFEAK-GLGAVIWNSGALMTQIQWFRDLKPFFCNTT
SEQ ID NO:26        RHSKGNDTFGVNFAVAGSTAINHLFFVKH-NLSLDI-TAQSIQTQMIWFNRYLESQ-ECQ
SEQ ID NO:28        EKTGQFRT-GANFAVLGSIALSPDYYSKRYNFSMPHW---CLDWELGSFKAVLARI-APG
SEQ ID NO:30        AHGKDFKK-GANFAITGATALEYSFFKAH-GIDQRIWNTGSINTQIGWLQKMKPSLCKSE
SEQ ID NO:32        TNGTDFRK-GANMAIIGATAMNLDFFQSH-GLGSSIWNNGPLDTQIQWFLQLMPSIC-GG
SEQ ID NO:34        -RGEDVRQ-GVNFEAVGGATAMDPPFFEGI-GASDKLWTNLSLSVQLDWFDKLKPSLCGSP
SEQ ID NO:36        --GADFKQ-GANMAIIGATAMGSSFFQSL-GVGDKIWNNGPLDTQIQWFQNLLPSVC-GS
SEQ ID NO:38        --SADFKK-GANMAITGATAMDAPFFRSL-GLSDKIWNNGPISFQLQWFQTITSSVC-GS
                    121
```

Figure 1 (page 4 of 7)

```
                     ***  *  **                                                             *
SEQ ID NO:39  SPDCRDMIENAFILIGEIGGNDYNFPLFD-RKNIEEVKELVPLVITTISSAISELVDMGA
SEQ ID NO:40  TRDCKEMLGDSLILMGEIGGNDYNYPFFE-GKSINEIKELVPLIVKAISSAIVDLIDLGG
SEQ ID NO:41  Q-KV-SLFKDSLFWIGEIGGNDYAYTL-GSTVSSDTIREL---SISTFTRFLETLLNKGV
SEQ ID NO:2   KRDCAKKLKNALFFVGEIGGNDYNFALFE-GKTIAEVKNMVPQVIRMIKYATRRVIKYGA
SEQ ID NO:4   QA-CKKFFAKALFVVGEFGGNDYNAPLFA-GMGIPEAYKFMPDVIQGISDGIEALIAEGA
SEQ ID NO:8   KVECDEFYANSLFVVGEFGGNDYNAPLFA-GKGLEEAYKFMPDVIQAISDGIEQLIAEGA
SEQ ID NO:10  N--CKSYLANSLFVFGEFGGNDYNAMLFG-GYSADQASTYTSQIVDTISNGVEKLIAMGA
SEQ ID NO:14  KEECDNYFKNSLFLVGEIGGNDIN-ALIP-YKNITELREMVPSIVETIANTTSKLIEEGA
SEQ ID NO:16  SS-CKKVIGSSLFIVGEIGGNDYGYPLSE-TTAFGDLVTYIPQVISVITSAIRELIDLGA
SEQ ID NO:22  EA-CKKFFAKALFVVGEFGGNDYNAPLFA-GMGIPEAYKFMPDVIQGISDGIEALIAEGA
SEQ ID NO:26  ESKC-NDFDDTLEWFGEIGVNDYAYTL-GSTVSDETIRKL---AISSVSGALQTLLEKGA
SEQ ID NO:28  KAATKRLLSESLIIFGEIGGNDYNFWFYDRQRSRDTPYKYMPDIIARIGSGVQEVINLGA
SEQ ID NO:30  K-ECRDYFSKSLFVVGEFGGNDYNAPLFS-GVAFSEVKTYVPLVAKAIANGVEKLIELGA
SEQ ID NO:32  AGDCRSHLSKSLFILGEFGGNDYNAAIFG-GKSLDEVYTVPHIINKVTSGVETLIGLGA
SEQ ID NO:34  KS-CKKYFSRSLFLVGEIGGNDYNYAFFK-GKTLDDAKSYVPTVSSAIIDATERLIKAGA
SEQ ID NO:36  S--CKTYLSKSLFVLGELGGNDYNAQLFG-GYTPEQAAGQSPTIVDAIGAGAEKLIGLGA
SEQ ID NO:38  S--CKSYLANSLFIFGEFGGNDYNAMLFG-NYNTDQASTYAPQIVDTIGAGVEKLVAMGA
              181                                                         240
```

Figure 1 (page 5 of 7)

```
                          *           **                     *                         *                       *
SEQ ID NO:39   RTFLVPGNFPLGCSVAYLTLYETPNKEEYNPLTGCLTWLNDFSVYHNEQLQAELKRLRNL
SEQ ID NO:40   KTFLVPGGFPTGCSAAYLTLFQTVAEKDQDPLTGCYPLLNEFGEHHNEQLKTELKRLQKF
SEQ ID NO:41   KYMLVQGHPATGCLTLAMSLAAEDDRDS----LGCVQSANNQSYTHNLALQSKLKQLRIK
SEQ ID NO:2    TRVVIPGHFSLGCLPIYLTGFQTNDSTAYDEF-HCLKNLNNLSSYHNRKLKQAIKLLRKE
SEQ ID NO:4    VEMIVPGVMPTGCFPVYLNMLDEPKEG-YGPHSGCVRRYNTFSWVHNAHLKAMLEKLRAK
SEQ ID NO:8    RELIVPGVMPTGCFPVYLNMLDEPADG-YGPQSGCVRRYNTFSWVHNAHLKRMLEKLRPK
SEQ ID NO:10   VDVVVPGVLPIGCFPIYLTIYGTSSSSDYDSL-GCLKKFNDLSTNHNNQLKTKISALQSK
SEQ ID NO:14   VELVVPGNFPIGCNSAVLAIVNSEKKEDYDQF-GCLIAYNTFIEYYNEQLKKAIETLRKN
SEQ ID NO:16   VTFMVPGSLPLGCNPAYLTFATIDKEEYDQ-AGCLKWLNTFYEYHNELLQIEINRLRVL
SEQ ID NO:22   VEMIVPGVMPTGCFPVYLNMLDEPKEG-YGPHSGCVRRYNTFSWVHNAHLKAMLEKLRAK
SEQ ID NO:26   KYLVVQGMPLTGCLTLSMYLAPPDDRDD----IRCVKSVNNQSYYHNLVLQDKLQEFRKQ
SEQ ID NO:28   KTILVPGNFPIGCVPIYLSGHKTNKSADYDQF-GCLKWYNTFSQKHNQMLRQEVGRLRSR
SEQ ID NO:30   TDLLVPGILPIGCFPLYLTLYNSSKKSDYNARTGCLRRYNRLAFHHNRELKQQLDALQKK
SEQ ID NO:32   VDVVVPGVLPIGCFPLYLTLYGSSNQSDYDGD-GCLRRFNDLSGYHNRLLRQGIGRLRSK
SEQ ID NO:34   MHLVVPGNLPMGCSSAYLTLHPGRSRSDYDA-VGCLRTYNDFAQRHNAMVQQKLQVLRLK
SEQ ID NO:36   MYVVIPGVLPVGCFPIYLTLYQTSNAGDYDQY-GCLKRFNALSARHNSLLQSKVTSLQGK
SEQ ID NO:38   VDVVVPGVLPIGCFPIYLTIYGTSSAADYDSL-GCLKKFNDLSTYHNSLLQAKVSALQAK
              241                                                        300
```

Figure 1 (page 6 of 7)

```
                         *            *             ***                *                  *
SEQ ID NO:39   YPHVNIIYGDYYNTLLRLMQEPSKFGLMDR----PLPACCGLGG-----PYNFTFSIKCGS
SEQ ID NO:40   YPHVNIIYADYHNSLYRFYQEPAKYGFKNK----PLAACCGVGG-----KYNFTIGKECGY
SEQ ID NO:41   YPSATIVYADYWNAYRAVIKHPSKYGIT-----EKFKACCGIGEP----YNFQVFQTCGT
SEQ ID NO:2    NPNVIITYGDYYNALFWIFQHASLLGF--DKISLQKSCCGAGGD-----YNFNIMQMCGF
SEQ ID NO:4    HPNVRIIYGDYYTPVVQFMLQPEKFGFARQ---LPRACCGXPSTPERAAYNFNVTAKCGE
SEQ ID NO:8    HPNVRIIYGDYYTPVIQFMLQPEKFGFYKQ---LPRACCGAPGSVAKAAYNFNVTAKCGE
SEQ ID NO:10   YKSARIMYADFYSGVYDMVRNPGNYGFSTV---F-ETCCGSGG-----GKFNYNNNARCGM
SEQ ID NO:14   NAHVKITYFDYYGATKRLFQAPQQYGFSSGKTETFRACCGKGEP-----YNLSFQILCGS
SEQ ID NO:16   YPLTNIIYADYFNAALEFYNSPEQFGFGGN---VLKVCCGGGG-----PYNYNETAMCGD
SEQ ID NO:22   HPNVRIIYGDYYTPVVQFMLQPEKFGFARQ---LPRACCGAPSTPERAAYNFNVTAKCGE
SEQ ID NO:26   YPQAVILYADYYDAYRTVMKNPSKYGFK-----ETFNVCCGSGEPP---YNFTVFATCGT
SEQ ID NO:28   NPGVKVIYADYYGAAMEFFRNPKRHGID----DPLVACCGGNGP-----YGTGRGCDQ
SEQ ID NO:30   YPKTKIMYGDYFKAAMQFVVSPGKFGFSTA---L-QACCGAGGT--GAYNFNLKKKCGE
SEQ ID NO:32   YAGVRLMYGDFYTQVAEMVRSPRSFGLDYG---L-TVCCGASG---QGSYNYNNKARCGM
SEQ ID NO:34   YPKARIMYADYYGAAMSFAKNPKQFGFKQG---PLKTCCGGGG-----PYNFNPKASCGV
SEQ ID NO:36   YPYAKIMYADFYSHVFDMVKSPASYGFSTN---L-RACCGAGG-----GKYNYQNGARCGM
SEQ ID NO:38   YKSARIMYADFYAGVYDMVQSPSKYGFSSV---F-EACCGSGG-----GKYNYANSARCGM
               301                                                         360
```

Figure 1 (page 7 of 7)

```
                      361                                                                              420
SEQ ID NO:39   KGVEYCSDPSKYVNWDGIHMTEAAYKWISEGVLTGPYAIPPFNWSCL-DSKIKNNESLHTQYSLMNS
SEQ ID NO:40   EGVNYCQNPSEYVNWDGYHLTEAAYQKMTEGILNGPYATPAFDWSCL-GS----------GTVDT
SEQ ID NO:41   DAATVCKDPNQYINWDGVHLTEAMYKVMADMFLDGTFTRPRFSD--LLIKKLN---------YL
SEQ ID NO:2    PGVPTCSNPNKRISWDGIHLTQKTYQYMAHRLVHDLF------P-------------KFHCTN-
SEQ ID NO:4    PGATACADPTTHWSWDGIHLTEAAYRHIAKGWLYGPFXDQPI-------------------IQSS
SEQ ID NO:8    AGATACDDPSTHWSWDGIHLTEAAYGHIARGWVYGPFADQPI-------------------FQSS
SEQ ID NO:10   SGASACSNPASHLSWDGIHLTEAAYKQITDGWLNGPYCSPAI-------------------LHS-
SEQ ID NO:14   PAAIVCSDPSKQINWDGPHFTEAAYRLIAKGLVEGPFANPSLKSP--------------PFK-IA-
SEQ ID NO:16   AGVVACDDPSQYVSWDGYHLTEAAYRWMTKGLLDGPYTIPKFNVSCFIGETIRDFNNYAMKYKSM-
SEQ ID NO:22   PGATACADPTTHWSWDGIHLTEAAYRHIAKGWLYGPFADQPI-------------------IQSS
SEQ ID NO:26   PNATVCSSPSQYINWDGVHLTEAMYKVISSMFLQGNFTQPPFNF--LLEKKER----------VG
SEQ ID NO:28   NA-KVCRDPSRFANWDQVHMTEKAYSVIANGVLNGPYADIPLLHAC-------------------
SEQ ID NO:30   AGASVCSNPSAYVSWDGIHMTEAAYRMVANGWLNGPYASPPI-------------------MK--
SEQ ID NO:32   SGSSACKDPQNYLNWDGIRLTEHAYRSIAYGWLTGPYCVPAI-------------------LH--
SEQ ID NO:34   RGSSVCADPSAYANWDGVHLTEAAYHAIADSILHGPYTSPRL-------------------L---
SEQ ID NO:36   SGASACGNPSSSLSWDGIHLTEAAYKKIADGWVNGPYCHPAI-------------------L-S-
SEQ ID NO:38   SGASACASPASHLSWDGIHLTEAAYKQITDGWLNGAFCHPGI-------------------TH--
```

PLANT LIPASES

This application claims priority benefit of U.S. Provisional Application No. 60/157,309 filed Oct. 1, 1999, now pending.

FIELD OF THE INVENTION

This invention is in the field of plant molecular biology. More specifically, this invention pertains to nucleic acid fragments encoding lipases in plants and seeds.

BACKGROUND OF THE INVENTION

True lipases act at an oil-water interface; they constitute a ubiquitous group of enzymes catalyzing a wide variety of reactions, many with industrial potential. Lipases have been grouped into families according to their amino acid sequence, enzymatic specificity, and differential expression. A family of lipolytic enzymes with members in *Arabidopsis thaliana*, rice and corn has been described (Brick et al. (1995) *FEBS Lett.* 377:475–480).

It is possible to change the structure of fats and oils by manipulating the lipase specificity ending with products containing the desired fatty acid at a specific position on the glycerol backbone. Lipases play important roles in pathogen defense and in activating membrane formation.

The lipase sequences presented herein also contain similarities to the alfalfa early nodule-specific gene ENOD8, which is activated soon after rhizobium infection. Corn and rice EST sequences having similarities to lipases that are found in the NCBI database having General Identifier Nos. 569288, 570021, 702247, 3763803, 3763804, 3768136, 4715132, 4716417, 4827484, 5455457, 5455577, 5455582, and 5455586.

Identification of cDNAs encoding lipases in crops will allow their manipulation, and thus, the creation of plants with oils of different fatty acid composition.

SUMMARY OF THE INVENTION

The present invention concerns an isolated polynucleotide comprising a nucleotide sequence selected from the group consisting of: (a) a first nucleotide sequence encoding a polypeptide of at least 157 amino acids having at least 80% identity based on the Clustal method of alignment when compared to a polypeptide selected from the group consisting of SEQ ID NOs:2, 4, 6, and 8, or (b) a second nucleotide sequence comprising the complement of the first nucleotide sequence.

In a second embodiment, it is preferred that the isolated polynucleotide of the claimed invention comprises a first nucleotide sequence which comprises a nucleic acid sequence selected from the group consisting of SEQ ID NOs:1, 3, 5, 7, 9, 11, 13, 15, 17, 19, 21, 23, 25, 27, 29, 31, 33, 35, and 37 that codes for the polypeptide selected from the group consisting of SEQ ID NOs:2, 4, 6, 8, 10, 12, 14, 16, 18, 20, 22, 24, 26, 28, 30, 32, 34, 36, 38, 40.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns a lipase polypeptide of at least 157 amino acids comprising at least 80% identity based on the Clustal method of alignment compared to a polypeptide selected from the group consisting of SEQ ID NOs:2, 4, 6, 8, 10, 12, 14, 16, 18, 20, 22, 24, 26, 28, 30, 32, 34, 36, 38, 40.

In an eighth embodiment, the invention relates to a method of selecting an isolated polynucleotide that affects the level of expression of a lipase polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the lipase polypeptide or enzyme activity in the host cell containing the isolated polynucleotide; and (d) comparing the level of the lipase polypeptide or enzyme activity in the host cell containing the isolated polynucleotide with the level of the lipase polypeptide or enzyme activity in the host cell that does not contain the isolated polynucleotide.

In a ninth embodiment, the invention concerns a method of obtaining a nucleic acid fragment encoding a substantial portion of a lipase polypeptide, preferably a plant lipase polypeptide, comprising the steps of: synthesizing an oligonucleotide primer comprising a nucleotide sequence of at least one of 60 (preferably at least one of 40, most preferably at east one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a lipase amino acid sequence.

In a tenth embodiment, this invention relates to a method of obtaining a nucleic acid fragment encoding all or a substantial portion of the amino acid sequence encoding a lipase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the lipase polynucleotide in an amount sufficient to complement a null mutant to provide a positive selection means.

In a thirteenth embodiment, this invention relates to a method of altering the level of expression of a lipase in a host cell comprising: (a) transforming a host cell with a chimeric gene of the present invention; and (b) growing the transformed host cell under conditions that are suitable for expression of the chimeric gene wherein expression of the chimeric gene results in production of altered levels of the lipase in the transformed host cell.

BRIEF DESCRIPTION OF THE DRAWINGS AND SEQUENCE LISTINGS

The invention can be more fully understood from the following detailed description and the accompanying drawings and Sequence Listing, which form a part of this application.

FIGS. 1A, 1B, 1C, 1D, 1E, 1F and 1G show a comparison of the amino acid sequences of the lipases derived from balsam pear clone fds.pk0019.d2:fis (SEQ ID NO:2), corn contig assembled from clones cco1n.pk068.n1, cr1.pk0027.g10, cr1s.pk016.g5, cta1n.pk0055.h3, ctn1c.pk002.i10, p0018.chssz33r, p0018.chstr42r, p0031.ccmbo06r, p0036.cmtaj12r, and p0051.cfbbb40r (SEQ ID NO:4), rice clone res1c.pk007.n1:fis (SEQ ID NO:8), rice contig assembled from clones rds3c.pk001.p14, rds3c.pk004.g24, res1c.pk008.i11, r10n.pk0044.g8, r1r6.pk0029.h3, r1s6.pk0079.b5, r1s72.pk0013.h6, and rr1.pk080.h15 (SEQ ID NO:10), soybean clone sfi1.pk0065.b6:fis (SEQ ID NO:14), soybean clone src1c.pk003.h4:fis (SEQ ID NO:16), corn clone ctn1c.pk002.i10:fis (SEQ ID NO:22), soybean clone sdp2c.pk019,i3:fis (SEQ ID NO:26), wheat clone wdk1c.pk0003.h2:fis (SEQ ID NO:28), wheat clone wdk1c.pk023.m3:fis (SEQ ID NO:30), wheat clone wdk9n.pk001.k24:fis (SEQ ID NO:32), wheat clone wle1.pk0001.d6:fis (SEQ ID NO:34), wheat clone wle1n.pk0009.e6;fis (SEQ ID NO:36), and wheat clone wlm24.pk0027.a6:fis (SEQ ID NO:38) with the *Arabidopsis thaliana* lipase sequences having NCBI General Identifier Nos. 4314378 (SEQ ID NO:39), 2129636 (SEQ ID NO:40), and 4678342 (SEQ ID NO:41). The putative active Ser is indicated with white letters in a black box while the amino acids conserved among all sequences are indicated with an asterisk (*) above the alignment. Dashes are used by the program to maximize the alignment.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Plant Lipases

| Protein | Clone Designation | SEQ ID NO: (Nucleotide) | SEQ ID NO: (Amino Acid) |
|---|---|---|---|
| Balsam Pear Lipase | fds.pk0019.d2:fis | 1 | 2 |
| Corn Lipase | Contig of:<br>cco1n.pk068.n1<br>cr1.pk0027.g10<br>cr1s.pk016.g5<br>cta1n.pk0055.h3<br>ctn1c.pk002.i10<br>p0018.chssz33r<br>p0018.chstr42r<br>p0031.ccmbo06r<br>p0036.cmtaj12r<br>p0051.cfbbb40r | 3 | 4 |
| Corn Lipase | Contig of:<br>cen3n.pk0015.a7<br>p0062.cymah73ra<br>p0062.cymal25r<br>p0100.cbaad10r<br>p0107.cbcas86r<br>p0107.cbcbc04r | 5 | 6 |
| Rice Lipase | res1c.pk007.nl:fis | 7 | 8 |
| Rice Lipase | Contig of:<br>rds3c.pk001.p14<br>rds3c.pk004.g24<br>res1c.pk008.i11<br>rl0n.pk0044.g8<br>rlr6.pk0029.h3<br>rls6.pk0079.b5<br>rls72.pk0013.h6<br>rr1.pk080.h15 | 9 | 10 |
| Soybean Lipase | sdp2c.pk019.i3 | 11 | 11 |
| Soybean Lipase | sfi1.pk0065.b6:fis | 13 | 14 |
| Soybean Lipase | src1c.pk003.h4:fis | 15 | 16 |
| Wheat Lipase | Contig of:<br>wlk1.pk0019.a2<br>wlm0.pk0025.g4<br>wlm24.pk0027.a6 | 17 | 18 |
| Wheat Lipase | Contig of:<br>wl1n.pk0078.d12<br>wl1n.pk151.b11<br>wre1n.pk0007.h7<br>wre1n.pk0044.b9 | 19 | 20 |
| Corn Lipase | ctn1c.pk002.i10:fis | 21 | 22 |
| Corn Lipase | p0107.cbcas86r:fis | 23 | 24 |
| Soybean Lipase | sdp2c.pk019.i3:fis | 25 | 26 |
| Wheat Lipase | wdk1c.pk0003.h2:fis | 27 | 28 |
| Wheat Lipase | wdk1c.pk023.m3:fis | 29 | 30 |
| Wheat Lipase | wdk9n.pk001.k24:fis | 31 | 32 |
| Wheat Lipase | wle1.pk0001.d6:fis | 33 | 34 |
| Wheat Lipase | wle1n.pk0009.e6:fis | 35 | 36 |
| Wheat Lipase | wlm24.pk0027.a6:fis | 37 | 38 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs:1, 3, 5, 7, 9, 11, 13, 15, 17, 19, 21, 23, 25, 27, 29, 31, 33, 35, and 37, or the complement of such sequences.

The term "isolated" polynucleotide refers to a polynucleotide that is substantially free from other nucleic acid sequences, such as and not limited to other chromosomal and extrachromosomal DNA and RNA that normally accompany or interact with the isolated polynucleotide as found in its naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37, and the complement of such nucleotide sequences may be used in methods of selecting an isolated polynucleotide that affects the expression of a lipase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene"is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15: 1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236). "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA " refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) first nucleotide sequence encoding a polypeptide of at least 157 amino acids having at least 80% identity based on the Clustal method of alignment when compared to a polypeptide selected from the group consisting of SEQ ID NOs:2, 4, 6, 8, 10, 12, 14, 16, 18, 20, 22, 24, 26, 28, 30, 32, 34, 36, 38, 40, or (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 9, 11, 13, 15, 17, 19, 21, 23, 25, 27, 29, 31, 33, 35, and 37.

Nucleic acid fragments encoding at least a portion of several lipases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other lipases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, and 37 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a lipase polypeptide, preferably a substantial portion of a plant lipase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15, 17, 19,21, 23, 25, 27, 29, 31, 33, 35, and 37, and the complement of such nucleotide sequences; and amplifying a nucleic acid fragment (preferably a cDNA inserted in a cloning vector) using the oligonucleotide primer. The amplified nucleic acid fragment preferably will encode a portion of a lipase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) Adv. Immunol. 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of lipid synthesis and may effect intra-plant signaling and/or defense responses in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) EMBO J. 4:2411–2418; De Almeida et al. (1989) Mol. Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), or nuclear localization signals (Raikhel (1992) Plant Phys. 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 157 amino acids that has at least 80% identity based on the Clustal method of alignment when compared to a polypeptide selected from the group consisting of SEQ ID NOs:2, 4, 6, 8, 10, 12, 14, 16, 18, 20, 22, 24, 26, 28, 30, 32, 34, 36, 38, 40.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded lipases. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from various balsam pear, corn, rice, soybean, and wheat tissues tissues were prepared. The characteristics of the libraries are described below.

TABLE 2 cDNA Libraries from Balsam Pear, Corn, Rice, Soybean, and Wheat

| Library | Tissue | Clone |
|---|---|---|
| cco1n | Corn Cob of 67 Day Old Plants Grown in Green House* | cco1n.pk068.n1 |
| cen3n | Corn Endosperm 20 Days After Pollination* | cen3n.pk0015.a7 |
| cr1 | Corn Root From 7 Day Old Seedlings | cr1.pk0027.g10 |
| cr1s | Corn Root From 7 Day Old Etiolated Seedlings | cr1s.pk016.g5 |
| cta1n | Corn Tassel* | cta1n.pk0055.h3 |
| ctn1c | Corn Tassel, Night Harvested | ctn1c.pk002.i10 |

TABLE 2-continued cDNA Libraries from Balsam Pear, Corn, Rice, Soybean, and Wheat

| Library | Tissue | Clone |
|---|---|---|
| fds | *Momordica charantia* developing seed | fds.pk0019.d2 |
| p0018 | Corn Seedling After 10 Day Drought, Heat Shocked for 24 Hours, Harvested After Recovery at Normal Growth Conditions for 8 Hours | p0018.chssz33r p0018.chstr42r |
| p0031 | Corn Shoot Culture | p0031.ccmbo06r |
| p0036 | Corn Tassels 16–18 cm Long | p0036.cmtaj12r |
| p0051 | Corn Middle 3/4 of the 3rd Leaf Blade and Mid rib from Green Leaves Treated with Jasmonic Acid (1 mg/ml in 0.02% Tween 20) 24 Hours Before Collection* | p0051.cfbbb40r |
| p0062 | Corn Coenocytic Embryo Sacs 4 Days After Pollination | p0062.cymah73ra p0062.cymal25r |
| p0100 | Corn Coenocytic Embryo Sacs 4 Days After Pollination* | p0100.cbaad10r |
| p0107 | Corn Whole Kernels 7 Days After Pollination* | p0107.cbcas86r p0107.cbcbc04r |
| rds3c | Rice Developing Seeds From Top of the Plant | rds3c.pk001.p14 rds3c.pk004.g24 |
| res1c | Rice Etiolated Seedling | res1c.pk007.n1 res1c.pk008.i11 |
| rl0n | Rice 15 Day Old Leaf* | rl0n.pk0044.g8 |
| rlr6 | Rice Leaf 15 Days After Germination, 6 Hours After Infection of Strain *Magaporthe grisea* 4360-R-62 (AVR2-YAMO); Resistant | rlr6.pk0029.h3 rls6.pk0079.b5 |
| rls72 | Rice Leaf 15 Days After Germination, 72 Hours After Infection of Strain *Magaporthe grisea* 4360-R-67 (AVR2-YAMO); Susceptible | rls72.pk0013.h6 |
| rr1 | Rice Root of Two Week Old Developing Seedling | rr1.pk080.h15 |
| sdp2c | Soybean Developing Pods (6–7 mm) | sdp2c.pk019.i3 |
| sfl1 | Soybean Immature Flower | sfl1.pk0065.b6 |
| src1c | Soybean 8 Day Old Root Infected With Cyst Nematode | src1c.pk003.h4 |
| wdk1c | Wheat Developing Kernel, 3 Days After Anthesis | wdk1c.pk0003.h2 wdk1c.pk023.m3 |
| wdk9n | Wheat Kernels 3, 7, 14 and 21 Days After Anthesis | wdk9n.pk001.k24 |
| wl1n | Wheat Leaf From 7 Day Old Seedling* | wl1n.pk0078.d12 wl1n.pk151.b11 |
| wle1 | Wheat Leaf From 7 Day Old Etiolated Seedling | wle1.pk0001.d6 |
| wle1n | Wheat Leaf From 7 Day Old Etiolated Seedling* | wle1n.pk0009.e6 |
| wlk1 | Wheat Seedlings 1 Hour After Treatment With Herbicide** | wlk1.pk0019.a2 |
| wlm0 | Wheat Seedlings 0 Hour After Inoculation With *Erysiphe graminis f.* sp *tritici* | wlm0.pk0025.g4 |
| wlm24 | Wheat Seedlings 24 Hours After Inoculation With *Erysiphe graminis f.* sp *tritici* | wlm24.pk0027.a6 |
| wre1n | Wheat Root From 7 Day Old Etiolated Seedling* | wre1n.pk0007.h7 wre1n.pk0044.b9 |

*These libraries were normalized essentially as described in U.S. Pat. No. 5,482,845, incorporated herein by reference.
**Application of 6-iodo-2-propoxy-3-propyl-4(3H)-quinazolinone; synthesis and methods of using this compound are described in U.S. Pat. No. 5,747,497, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

Example 2

Identification of cDNA Clones cDNA clones encoding lipases were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Lipases

The BLASTX search using the EST sequences from clones listed in Table 3 revealed similarity of the polypeptides encoded by the DNAs to a putative lipase, a lipase and a lipase-like protein from *Arabidopsis thaliana* (NCBI General Identifier Nos. 4314378, 2129636 and 4678342, respectively). The first and last polypeptides are the result of genomic sequencing projects and have been identified by similarity with known lipases. Shown in Table 3 are the BLAST results for individual ESTs ("EST"), the sequences of the entire cDNA inserts comprising the indicated cDNA clones ("FIS"), or the sequences of contigs assembled from two or more ESTs ("Contig"). Sequences where the item under "Status" appears marked with an asterisk (*) encode an entire protein:

TABLE 3

BLAST Results for Sequences Encoding Polypeptides Homologous to Lipases

| | | BLAST pLog Score | | |
|---|---|---|---|---|
| Clone | Status | 4314378 | 2129636 | 4678342 |
| fds.pk0019.d2 | FIS* | 68.22 | 70.10 | 53.10 |
| Contig of:<br>cco1n.pk068.n1<br>cr1.pk0027.g10<br>cr1s.pk016.g5<br>cta1n.pk0055.h3<br>ctn1c.pk002.i10<br>p0018.chssz33r<br>p0018.chstr42r<br>p0031.ccmbo06r<br>p0036.cmtaj12r<br>p0051.cfbbb40r | Contig* | 70.30 | 66.10 | 44.00 |
| Contig of:<br>cen3n.pk0015.a7<br>p0062.cymah73ra<br>p0062.cymal25r<br>p0100.cbaad10r<br>p0107.cbcas86r<br>p0107.cbcbc04r | Contig* | 58.52 | 57.70 | 47.53 |
| res1c.pk007.nl | FIS* | 74.70 | 69.52 | 41.70 |
| Contig of:<br>rds3c.pk001.p14<br>rds3c.pk004.g24<br>res1c.pk008.i11<br>r10n.pk0044.g8<br>rlr6.pk0029.h3<br>rls6.pk0079.b5<br>r1s72.pk0013.h6<br>rr1.pk080.h15 | Contig* | 67.40 | 70.10 | 52.70 |
| sdp2c.pk019.i3 | EST | 20.52 | 22.00 | 51.15 |
| sfl1.pk0065.b6 | FIS* | 79.22 | 74.52 | 54.40 |
| src1c.pk003.h4 | FIS* | 108.00 | 103.00 | 60.70 |
| Contig of:<br>wlk1.pk0019.a2<br>wlm0.pk0025.g4<br>w1m24.pk0027.a6 | Contig | 13.70 | 10.52 | 11.70 |
| Contig of:<br>wl1n.pk0078.d12<br>wl1n.pk151.b11<br>wre1n.pk0007.h7<br>wre1n.pk0044.b9 | Contig | 35.00 | 27.10 | 18.70 |

The rice contig assembled from clones rds3c.pk001.p14, rds3c.pk004.g24, res1c.pk008.i11, r10n.pk0044.g8, r1r6.pk0029.h3, r1s6.pk0079.b5, r1s72.pk0013.h6 and rr1.pk080.h15 also revealed similarity of the polypeptides encoded by the cDNAs to a protein similar to putative lipase from *Medicago truncatula* (NCBI General Identifier No. 5734636) with a pLog value of 60.22. The wheat contig assembled from clones wlk1.pk0019.a2, wlm0.pk0025.g4 and wlm24.pk0027.a6 also revealed similarity of the polypeptides encoded by the cDNAs to "similar to putative lipase" from *Oryza sativa* (NCBI General Identifier No. 5734634) with a pLog value of 28.52; a "similar to nodulins and lipase homolog" from *Arabidopsis thaliana* (NCBI General Identifier No. 3776573) with a pLog value of 12.52; and to "similar to the GDSL family of lipolytic enzymes" from *Arabidopsis thaliana* (NCBI General Identifier No. 2191137) with a pLog value of 11.00.

The sequence of the entire cDNA insert in clones ctn1c.pk002.i10, p0107.cbcas86r, sdp2c.pk019.i3, and wlm24.pk0027.a6 was determined. Further sequencing and searching of the DuPont proprietary database allowed the identification of other wheat clones encoding lipase homologs.

The BLASTX search using the EST sequences from clones listed in Table 4 revealed similarity of the polypeptides encoded by the contigs to putative lipases, lipase-like protein, and BAC FIK23.15 from *Arabidopsis thaliana* (NCBI General Identifier Nos. 4314378, 5306262, 4678342, and 6691210, respectively), and by the contigs to similar to lipases from *Oryza sativa* (NCBI General Identifier Nos. 7523500 and 7523511). The polypeptides disclosed in NCBI General Identifier Nos. 4314378, 5306262 are 100% identical and were disclosed to the public on Mar. 2, 1999 and Apr. 5, 2000, respectively. The polypeptide disclosed in NCBI General Identifier No. 6691210 appears to be a chimera containing 406 additional amino acids at the N-terminus of the putative lipase-like protein. Shown in Table 4 are the BLAST results for the sequences of the entire cDNA inserts comprising the indicated cDNA clones encoding the entire protein ("CGS"):

TABLE 4

BLAST Results for Sequences Encoding Polypeptides Homologous to Lipases

| Clone | Status | NCBI General Identifier No. | BLAST pLog Score |
|---|---|---|---|
| ctn1c.pk002.i10:fis | CGS | 4314378 | 72.30 |
| p0107.cbcas86r:fis | CGS | 5306262 | 64.00 |
| sdp2c.pk019.i3:fis | CGS | 4678342 | 132.00 |
| wdk1c.pk0003.h2:fis | CGS | 6691210 | 76.00 |
| wdk1c.pk023.m3:fis | CGS | 7523511 | 121.00 |
| wdk9n.pk001.k24:fis | CGS | 5306262 | 76.00 |
| wle1.pk0001.d6:fis | CGS | 7523500 | >180.00 |
| wle1n.pk0009.e6:fis | CGS | 7523511 | 137.00 |
| wlm24.pk0027.a6:fis | CGS | 5306262 | 71.10 |

FIGS. 1A, 1B, 1C, 1D, 1E, 1F and 1G present an alignment of the amino acid sequences set forth in SEQ ID NOs:2, 4, 8, 10, 14, 16, 22, 26, 28, 30, 32, 34, 36, and 38 and the *Arabidopsis thaliana* lipase sequences (NCBI General Identifier No. 4314378, SEQ ID NO:39, NCBI General Identifier No. 2129636, SEQ ID NO:40, and NCBI General Identifier No. 4678342, SEQ ID NO:41). The putative active Ser is indicated with white letters in a black box while the amino acids conserved among all the sequences are indicated with an asterisk (*) above the alignment. The amino acid sequences set forth in SEQ ID NO:6 and in SEQ ID NO:24 show homology to GDSL-type lipases but do not have the active-site serine. These sequences have instead GDDT.

The data in Table 5 presents a calculation of the percent identity of the amino acid sequences set forth in SEQ ID NOs:2, 4, 6, 8, 10, 12, 14, 16, 18, 20, 22, 24, 26, 28, 30, 32, 34, 36, and 38 and the *Arabidopsis thaliana* sequences having NCBI General Identifier Nos. 4314378, 2129636 and 4678342.

TABLE 5

Percent Identity of Amino Acid Sequences Deduced From the Nucleotide Sequences of cDNA Clones Encoding Polypeptides Homologous to Lipases

| | Percent Identity to | | |
|---|---|---|---|
| SEQ ID NO. | 4314378 | 2129636 | 4678342 |
| 2 | 34.8 | 35.3 | 27.7 |
| 4 | 34.1 | 32.0 | 24.9 |
| 6 | 29.7 | 30.0 | 26.9 |
| 8 | 35.3 | 33.0 | 23.1 |
| 10 | 313.0 | 32.9 | 27.7 |
| 12 | 32.5 | 33.8 | 54.8 |
| 14 | 37.6 | 35.8 | 28.2 |
| 16 | 45.2 | 44.5 | 31.0 |
| 18 | 24.7 | 26.8 | 25.8 |
| 20 | 37.9 | 31.3 | 25.3 |
| 22 | 34.9 | 32.5 | 24.9 |
| 24 | 32.1 | 31.9 | 28.5 |
| 26 | 32.1 | 31.6 | 58.2 |
| 28 | 33.7 | 32.6 | 28.1 |
| 30 | 37.9 | 37.1 | 26.8 |
| 32 | 35.0 | 31.4 | 25.8 |
| 34 | 38.4 | 39.7 | 30.3 |
| 36 | 33.0 | 35.5 | 30.2 |
| 38 | 33.7 | 32.9 | 30.4 |

Sequence alignments and percent identity calculations were performed using the Megalign program of the LASERGENE bioinformatics computing suite (DNASTAR Inc., Madison, Wis.) Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOWS=5 and DIAGONALS SAVED= 5. Sequence alignments and BLAST scores and probabilities indicate that the nucleic acid fragments comprising the instant cDNA clones encode balsam pear (one entire), corn (four entire), rice (two entire), soybean (one substantial portion and three entire), and wheat (two substantial portions and six entire) lipases.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having lipase activity, wherein the amino acid sequence of the polypeptide and the amino acid sequence of SEQ ID NO:2 have at least 90% sequence identity based on the Clustal method of alignment, or
   (b) a full-length complement of the nucleotide sequence of (a).

2. The polynucleotide of claim 1, wherein the polynucleotide comprises the nucleotide sequence of SEQ ID NO:1.

3. A transgenic plant comprising the polynucleotide of claim 1.

4. A method for transforming a cell comprising introducing into the cell the polynucleotide of claim 1.

5. A method for producing a transgenic plant comprising (a) transforming a plant cell with the polynucleotide of claim 1, and (b) regenerating a plant from the transformed plant cell.

6. A vector comprising the polynucleotide of claim 1.

7. A recombinant DNA construct comprising the polynucleotide of claim 1, operably linked to at least one regulatory sequence.

8. A cell comprising the recombinant DNA construct of claim 7.

9. The cell of claim 8, wherein the cell is selected from the group consisting of a yeast cell, a bacterial cell and a plant cell.

10. The polynucleotide of claim 1, wherein the amino acid sequence of the polypeptide and the amino acid sequence of SEQ ID NO:2 have at least 95% sequence identity based on the Clustal alignment method.

11. The polynucleotide of claim 1, wherein the amino acid sequence of the polypeptide comprises SEQ ID NO:2.

* * * * *

SEQUENCE LISTING

<160> NUMBER OF SEQ ID NOS: 41

<210> SEQ ID NO 1
<211> LENGTH: 1417
<212> TYPE: DNA
<213> ORGANISM: Momordica charantia

<400> SEQUENCE: 1

| | | | | | |
|---|---|---|---|---|---|
| gcacgaggca | ccaaaaagct | cattaatggc | ggttctgtgg | ggctgttat | ttattgttgt | 60 |
| tgttggtttt | ccatttgggt | gtaattgtga | ggttctgaag | aagtgtaaat | ttgatgccat | 120 |
| atatcagttc | ggggactctt | tggcagacac | tggaaatctg | ataagggaga | atcctcaaac | 180 |
| tcctttctct | cgtctccctt | atggccagac | cttcttcaac | aggcccactg | gcgttgttc | 240 |
| taatggcttg | ctcatgcttg | attatttttc | tttggcagct | gggctccctt | tggccaatcc | 300 |
| ctacttgaag | aaaaatgcat | ctttcacaca | tggagtgaat | tttgcggtgg | ctggctctac | 360 |
| cgctttgtct | ttcagagatc | tagctcaaat | gaacatctca | tctccggtta | ccaactcatc | 420 |
| tctgggtaaa | caacttgatt | ggatgcatac | acatctcaat | actatttgtt | gtaataaaag | 480 |
| agattgtgct | aagaagttaa | agaatgcatt | atttttgtt | ggcgagattg | gagggaatga | 540 |
| ttataatttt | gctctatttg | agggcaaaac | tatcgcggaa | gtgaaaaata | tggtgcctca | 600 |
| agttatcagg | atgataaaat | atgctactag | aagggtcatc | aagtatggtg | ctactcgagt | 660 |
| tgttattccg | ggacactttt | cactgggttg | cttaccaatc | tatctcaccg | gctttcaaac | 720 |
| caatgattca | accgcttacg | acgagtttca | ctgtttgaag | aatttaaata | acttatcaag | 780 |
| ttatcacaat | agaaaattga | agcaagcaat | caagctattg | agaaaagaga | atcctaatgt | 840 |
| gataattacc | tacggtgatt | attataatgc | gctattttgg | attttccaac | atgcttcttt | 900 |
| acttggattt | gataaaatat | cgctgcaaaa | gtcttgttgt | ggagctggag | gtgattataa | 960 |
| cttcaacatc | atgcaaatgt | gtggatttcc | aggagtacca | acttgttcta | atcctaataa | 1020 |
| acgcattagt | tgggatggaa | ttcatctgac | tcaaaagact | tatcaatata | tggcccatcg | 1080 |
| actcgtccat | gatctattcc | caaaatttca | ttgcacaaat | taaattaggt | aggtgtagct | 1140 |
| tattagtctt | agtaatatct | ttttccgttt | attttgttt | tagttaagaa | ggtttgtaat | 1200 |
| tttcatgaag | ataagattg | gatatactca | aatctaatca | atatcatgta | tattttcgt | 1260 |
| tacacatgca | tgtctattgc | caaagcgagt | atagctcaac | ggtaattgac | atatacctcc | 1320 |
| aaccaagaga | ttgtgagttt | gaatccccca | acatgtttac | taaaaaaaa | aaatgaatgc | 1380 |
| atgtctattt | tcttggaata | aaaaaaaaaa | aaaaaaa | | | 1417 |

<210> SEQ ID NO 2
<211> LENGTH: 365
<212> TYPE: PRT
<213> ORGANISM: Momordica charantia

<400> SEQUENCE: 2

Met Ala Val Leu Trp Gly Cys Leu Phe Ile Val Val Gly Phe Pro
  1               5                  10                  15

Phe Gly Cys Asn Cys Glu Val Leu Lys Lys Cys Lys Phe Asp Ala Ile
                 20                  25                  30

Tyr Gln Phe Gly Asp Ser Leu Ala Asp Thr Gly Asn Leu Ile Arg Glu
             35                  40                  45

Asn Pro Gln Thr Pro Phe Ser Arg Leu Pro Tyr Gly Gln Thr Phe Phe
         50                  55                  60

```
Asn Arg Pro Thr Gly Arg Cys Ser Asn Gly Leu Leu Met Leu Asp Tyr
 65                  70                  75                  80

Phe Ser Leu Ala Ala Gly Leu Pro Leu Ala Asn Pro Tyr Leu Lys Lys
                 85                  90                  95

Asn Ala Ser Phe Thr His Gly Val Asn Phe Ala Val Ala Gly Ser Thr
            100                 105                 110

Ala Leu Ser Phe Arg Asp Leu Ala Gln Met Asn Ile Ser Ser Pro Val
        115                 120                 125

Thr Asn Ser Ser Leu Gly Lys Gln Leu Asp Trp Met His Thr His Leu
    130                 135                 140

Asn Thr Ile Cys Cys Asn Lys Arg Asp Cys Ala Lys Lys Leu Lys Asn
145                 150                 155                 160

Ala Leu Phe Phe Val Gly Glu Ile Gly Gly Asn Asp Tyr Asn Phe Ala
                165                 170                 175

Leu Phe Glu Gly Lys Thr Ile Ala Glu Val Lys Asn Met Val Pro Gln
            180                 185                 190

Val Ile Arg Met Ile Lys Tyr Ala Thr Arg Arg Val Ile Lys Tyr Gly
        195                 200                 205

Ala Thr Arg Val Val Ile Pro Gly His Phe Ser Leu Gly Cys Leu Pro
    210                 215                 220

Ile Tyr Leu Thr Gly Phe Gln Thr Asn Asp Ser Thr Ala Tyr Asp Glu
225                 230                 235                 240

Phe His Cys Leu Lys Asn Leu Asn Asn Leu Ser Ser Tyr His Asn Arg
                245                 250                 255

Lys Leu Lys Gln Ala Ile Lys Leu Leu Arg Lys Glu Asn Pro Asn Val
            260                 265                 270

Ile Ile Thr Tyr Gly Asp Tyr Tyr Asn Ala Leu Phe Trp Ile Phe Gln
        275                 280                 285

His Ala Ser Leu Leu Gly Phe Asp Lys Ile Ser Leu Gln Lys Ser Cys
    290                 295                 300

Cys Gly Ala Gly Gly Asp Tyr Asn Phe Asn Ile Met Gln Met Cys Gly
305                 310                 315                 320

Phe Pro Gly Val Pro Thr Cys Ser Asn Pro Asn Lys Arg Ile Ser Trp
                325                 330                 335

Asp Gly Ile His Leu Thr Gln Lys Thr Tyr Gln Tyr Met Ala His Arg
            340                 345                 350

Leu Val His Asp Leu Phe Pro Lys Phe His Cys Thr Asn
        355                 360                 365

<210> SEQ ID NO 3
<211> LENGTH: 1540
<212> TYPE: DNA
<213> ORGANISM: Zea mays
<220> FEATURE:
<221> NAME/KEY: unsure
<222> LOCATION: (1180)
<223> OTHER INFORMATION: n = a, c, g or t
<220> FEATURE:
<221> NAME/KEY: unsure
<222> LOCATION: (1351)..(1352)
<223> OTHER INFORMATION: n = a, c, g or t
<220> FEATURE:
<221> NAME/KEY: unsure
<222> LOCATION: (1386)
<223> OTHER INFORMATION: n = a, c, g or t
<220> FEATURE:
<221> NAME/KEY: unsure
<222> LOCATION: (1388)
<223> OTHER INFORMATION: n = a, c, g or t
```

<220> FEATURE:
<221> NAME/KEY: unsure
<222> LOCATION: (1394)
<223> OTHER INFORMATION: n = a, c, g or t
<220> FEATURE:
<221> NAME/KEY: unsure
<222> LOCATION: (1397)
<223> OTHER INFORMATION: n = a, c, g or t
<220> FEATURE:
<221> NAME/KEY: unsure
<222> LOCATION: (1443)
<223> OTHER INFORMATION: n = a, c, g or t

<400> SEQUENCE: 3

| | | | | | |
|---|---|---|---|---|---|
| gagtgaacca | cgccaccaca | cgcagcgagc | gagcgcccaa | agaaacgccg | tagcagccac | 60 |
| caccaccacc | aaccccttcc | tcccttccc | tctccgccgc | ccgcctctct | acaagaaccc | 120 |
| tcacccgacc | gccgataact | acctagctcc | cacctcgctc | ctcgactccg | tcttctctat | 180 |
| tcttccattt | agcggagatc | ctagaaccta | ggggcagcca | gccaggggga | acgggccgcc | 240 |
| gaatgggagg | aagggcgcg | atgctcgctg | tggtgttggt | ggttcttgcg | gcggttggcg | 300 |
| ccgcggcgga | atcgatggag | gcggcagcca | agggaggta | ccacgcgctc | ttcaactttg | 360 |
| gggactcgct | agccgacgct | ggcaacctca | tccagaacgg | caccccggag | atcctggcca | 420 |
| ccgcgcgcct | gccctacggc | cagacctact | tcggcagggc | caccggccgc | tgctccgacg | 480 |
| gacgcctcgt | catcgaccac | ctcgcacaag | agtttggcct | gccgctgctg | ccgccgtcca | 540 |
| aggccacgaa | cgccagcttc | gcgtacggcg | ccaatttcgc | catcaccggc | gccaccgcgc | 600 |
| tcgacacgcc | ctacttcgag | gccaaggggc | tcggtgccgt | catctggaac | tccggagcgc | 660 |
| tcatgaccca | aatccagtgg | ttccgtgatc | tcaagccttt | cttctgcaac | acaacgcagg | 720 |
| catgcaagaa | attctttgcc | aaggcgctgt | ttgtggtcgg | tgagtttggc | ggcaatgact | 780 |
| acaatgcacc | cctcttttgcg | ggcatgggca | tccctgaggc | ctacaaattc | atgcccgatg | 840 |
| tcatacaggg | catctctgac | ggtattgagg | cactgattgc | tgaggggct | gttgagatga | 900 |
| ttgtgcctgg | tgtcatgccc | acgggctgct | tcccagttta | cttgaacatg | cttgatgagc | 960 |
| ccaaagaagg | atacggcccc | cacagtggtt | gtgtccgccg | gtacaacaca | ttctcctggg | 1020 |
| tgcacaatgc | acatcttaag | gccatgcttg | agaagctccg | ggctaagcac | ccaatgtga | 1080 |
| ggatcatata | tggcgattac | tacactccag | tcgtccagtt | catgcttcag | cctgagaagt | 1140 |
| ttggttttgc | cagacaactg | cccagggcat | gttgtggggn | gccatcgact | cctgagagag | 1200 |
| cagcttacaa | cttcaatgtc | acggccaaat | gcggtgagcc | tggtgcaact | gcctgtgctg | 1260 |
| atccgacaac | ccattggagc | tgggacggca | ttcacctgac | ggaggctgcc | taccgccata | 1320 |
| tcgccaaagg | ctggctatac | gggccttcg | nngaccaacc | gatcatccaa | tcctcatgat | 1380 |
| catgcngntc | ctgnggnaga | gtttatcaaa | gtagcattga | gagtgagaga | aaaaaaatgg | 1440 |
| agnggggaaa | gtaggtcttc | catacagttc | caatgcttgc | atacttgtac | atctccattt | 1500 |
| gattgtattc | atttgccatg | gggggtccaa | aggtgggata | | | 1540 |

<210> SEQ ID NO 4
<211> LENGTH: 378
<212> TYPE: PRT
<213> ORGANISM: Zea mays
<220> FEATURE:
<221> NAME/KEY: UNSURE
<222> LOCATION: (313)
<223> OTHER INFORMATION: Xaa = any amino acid
<220> FEATURE:
<221> NAME/KEY: UNSURE
<222> LOCATION: (370)

<223> OTHER INFORMATION: Xaa = any amino acid

<400> SEQUENCE: 4

```
Met Gly Gly Arg Gly Ala Met Leu Ala Val Val Leu Val Leu Ala
 1               5                  10                  15

Ala Val Gly Ala Ala Ala Glu Ser Met Glu Ala Ala Lys Gly Arg
                20                  25                  30

Tyr His Ala Leu Phe Asn Phe Gly Asp Ser Leu Ala Asp Ala Gly Asn
                35                  40                  45

Leu Ile Gln Asn Gly Thr Pro Glu Ile Leu Ala Thr Ala Arg Leu Pro
    50                  55                          60

Tyr Gly Gln Thr Tyr Phe Gly Arg Ala Thr Gly Arg Cys Ser Asp Gly
 65                  70                  75                  80

Arg Leu Val Ile Asp His Leu Ala Gln Glu Phe Gly Leu Pro Leu Leu
                85                  90                  95

Pro Pro Ser Lys Ala Thr Asn Ala Ser Phe Ala Tyr Gly Ala Asn Phe
                100                 105                 110

Ala Ile Thr Gly Ala Thr Ala Leu Asp Thr Pro Tyr Phe Glu Ala Lys
                115                 120                 125

Gly Leu Gly Ala Val Ile Trp Asn Ser Gly Ala Leu Met Thr Gln Ile
    130                 135                 140

Gln Trp Phe Arg Asp Leu Lys Pro Phe Phe Cys Asn Thr Thr Gln Ala
145                 150                 155                 160

Cys Lys Lys Phe Ala Lys Ala Leu Phe Val Val Gly Glu Phe Gly
                165                 170                 175

Gly Asn Asp Tyr Asn Ala Pro Leu Phe Ala Gly Met Gly Ile Pro Glu
                180                 185                 190

Ala Tyr Lys Phe Met Pro Asp Val Ile Gln Gly Ile Ser Asp Gly Ile
                195                 200                 205

Glu Ala Leu Ile Ala Glu Gly Ala Val Glu Met Ile Val Pro Gly Val
    210                 215                 220

Met Pro Thr Gly Cys Phe Pro Val Tyr Leu Asn Met Leu Asp Glu Pro
225                 230                 235                 240

Lys Glu Gly Tyr Gly Pro His Ser Gly Cys Val Arg Arg Tyr Asn Thr
                245                 250                 255

Phe Ser Trp Val His Asn Ala His Leu Lys Ala Met Leu Glu Lys Leu
                260                 265                 270

Arg Ala Lys His Pro Asn Val Arg Ile Ile Tyr Gly Asp Tyr Tyr Thr
                275                 280                 285

Pro Val Val Gln Phe Met Leu Gln Pro Glu Lys Phe Gly Phe Ala Arg
    290                 295                 300

Gln Leu Pro Arg Ala Cys Cys Gly Xaa Pro Ser Thr Pro Glu Arg Ala
305                 310                 315                 320

Ala Tyr Asn Phe Asn Val Thr Ala Lys Cys Gly Glu Pro Gly Ala Thr
                325                 330                 335

Ala Cys Ala Asp Pro Thr Thr His Trp Ser Trp Asp Gly Ile His Leu
                340                 345                 350

Thr Glu Ala Ala Tyr Arg His Ile Ala Lys Gly Trp Leu Tyr Gly Pro
    355                 360                 365

Phe Xaa Asp Gln Pro Ile Ile Gln Ser Ser
                370                 375
```

<210> SEQ ID NO 5
<211> LENGTH: 1201

```
<212> TYPE: DNA
<213> ORGANISM: Zea mays

<400> SEQUENCE: 5
ctagcaatac ttgaagatga acaaccatat ttccattcta gtgattctca tcgtcgatgt      60
gtctgttgtc ctcctgctca attcccatgt agggttatgc agctgctaca accgcatctt     120
tagtttggt gacgatacca tggacactgg aaatttcatt cacttgattg ggaaggcccc      180
atctaagtac aaggaagccc cctatggcaa gacatttttt agacatgcaa ctggccgcat     240
ttctgatggt cgtgtcctca ttgatttcta tgcggaagca ctaaaactgc caatgatacc     300
acccatttta cctgagaaga actttgggtg tttcccacat ggcgccaact tcgctgtgtt     360
tggtgccacg gcacgtgcaa aagtcttctt ttcaggagc ccctggtgta taggcacaca     420
aatgtactgg tttgatcaat tggtagatcg tatagctccc ggagatgctg ccaagaagca     480
atttctaagt gattctcttg tcattatggg tggaattggt caaatgact actactcata     540
tttcatcaaa ggtaaacctc ccaaggatgg aaatatcatt tcagatgtca tcgcagacat     600
aagccatttc atcgaggagc ttattgtcgt taatggggcg aaagcattcg tggtcgccaa     660
taactttccc gttgggtgtt tggcatcata cctaagtagg ttccacagtg acgaccatga     720
ggactacgat gagcatgggt gccttaagtc gttcaatgag ttctcccaaa agcataatga     780
gcaactttat tctgccatcg acaaatcag atactcttac ccaaatgtga aggtaatcta     840
tgctgactac tacaacgcca ccatggaatt catcaaaaaa cctaataaat ttggtattgg     900
tgatcctcta gtaccatgtt gtggcggcaa tggaccatac cacaccagca tggaatgcaa     960
tggcacagca aagctttggg gtgacccaca ccacttcccc aattgggatg gcatgcacat    1020
gacaaaaaag gctaccactc attatggaag ggtgttaaat gggcattgtg atcctccatt    1080
tccacttagt tgctaggatt agttacgcta ggaattcctt acaacatgta gccaatattt    1140
tttataataa tggaagtatt ttggatttat actacttcaa ggaagaagta actttcaaaa    1200
t                                                                    1201

<210> SEQ ID NO 6
<211> LENGTH: 360
<212> TYPE: PRT
<213> ORGANISM: Zea mays

<400> SEQUENCE: 6

Met Asn Asn His Ile Ser Ile Leu Val Ile Leu Ile Val Asp Val Ser
  1               5                  10                  15

Val Val Leu Leu Leu Asn Ser His Val Gly Leu Cys Ser Cys Tyr Asn
                 20                  25                  30

Arg Ile Phe Ser Phe Gly Asp Asp Thr Met Asp Thr Gly Asn Phe Ile
             35                  40                  45

His Leu Ile Gly Lys Ala Pro Ser Lys Tyr Lys Glu Ala Pro Tyr Gly
         50                  55                  60

Lys Thr Phe Phe Arg His Ala Thr Gly Arg Ile Ser Asp Gly Arg Val
     65                  70                  75                  80

Leu Ile Asp Phe Tyr Ala Glu Ala Leu Lys Leu Pro Met Ile Pro Pro
                 85                  90                  95

Ile Leu Pro Glu Lys Asn Phe Gly Cys Phe Pro His Gly Ala Asn Phe
                100                 105                 110

Ala Val Phe Gly Ala Thr Ala Arg Ala Lys Val Phe Phe Ser Gly Ser
            115                 120                 125
```

```
Pro Trp Cys Ile Gly Thr Gln Met Tyr Trp Phe Asp Gln Leu Val Asp
    130                 135                 140
Arg Ile Ala Pro Gly Asp Ala Ala Lys Lys Gln Phe Leu Ser Asp Ser
145                 150                 155                 160
Leu Val Ile Met Gly Ile Gly Gln Asn Asp Tyr Tyr Ser Tyr Phe
                165                 170                 175
Ile Lys Gly Lys Pro Pro Lys Asp Gly Asn Ile Ile Ser Asp Val Ile
            180                 185                 190
Ala Asp Ile Ser His Phe Ile Glu Glu Leu Ile Val Val Asn Gly Ala
                195                 200                 205
Lys Ala Phe Val Val Ala Asn Asn Phe Pro Val Gly Cys Leu Ala Ser
        210                 215                 220
Tyr Leu Ser Arg Phe His Ser Asp Asp His Glu Asp Tyr Asp Glu His
225                 230                 235                 240
Gly Cys Leu Lys Ser Phe Asn Glu Phe Ser Gln Lys His Asn Glu Gln
                245                 250                 255
Leu Tyr Ser Ala Ile Gly Gln Ile Arg Tyr Ser Tyr Pro Asn Val Lys
            260                 265                 270
Val Ile Tyr Ala Asp Tyr Tyr Asn Ala Thr Met Glu Phe Ile Lys Lys
        275                 280                 285
Pro Asn Lys Phe Gly Ile Gly Asp Pro Leu Val Pro Cys Cys Gly Gly
    290                 295                 300
Asn Gly Pro Tyr His Thr Ser Met Glu Cys Asn Gly Thr Ala Lys Leu
305                 310                 315                 320
Trp Gly Asp Pro His His Phe Pro Asn Trp Asp Gly Met His Met Thr
                325                 330                 335
Lys Lys Ala Thr Thr His Tyr Gly Arg Val Leu Asn Gly Pro Phe Ala
            340                 345                 350
Asp Pro Pro Phe Pro Leu Ser Cys
        355                 360

<210> SEQ ID NO 7
<211> LENGTH: 1750
<212> TYPE: DNA
<213> ORGANISM: Oryza sativa

<400> SEQUENCE: 7
gcacgaggca attactcccc aagccgcgag agagcccgag agtaaactaa tcgccatccg      60
ccaccgcgca gccgcggcag ctagctcgcg agaagaaaac gccacgcgac ccgagagcga     120
gagagagaga gagctaagcc gccgtgcgcc acgccaccac caccaaccca tcccaatctc     180
tctctctctc tctcctcgtg ctcctagcta caagaagaac cccctcaccc ccaccccgga     240
cacctaccta gccgctaccc ctctctcttc ctcttcttct tcttcttccc tcttcttgtg     300
gtggtgggtt tgacccaaga acggaggagg gatagggcgg gcggcgatgg gggcagttcg     360
ggggattttg gtcgtggcgg tggttcttgc ggtggcggcg attcttgctg ggcggcgga      420
ggggaaggtg aacgggaagg cgaagggggaa gtacagggcg ctgttcaact tcggggactc     480
gctggccgac gccggcaacc tcctcgccaa cggcgtcgac ttccgcctcg ctaccgccca     540
gctcccctac ggccagacct tccccggcca ccccaccggc cgctgctccg acggccgcct     600
cgtcgtcgac cacctcgccg acgagttcgg cctgccgctg ctgccgccgt ccaagctcaa     660
gaactccagc ttcgctcacg gcgccaactt cgccatcacc ggcgccaccg cgctcgacac     720
ccctacttc gaggccaagg ggctcggcgc cgtcgtctgg aactccggcg ccctcctcac     780
```

-continued

```
ccaaatccag tggttccgcg atctcaagcc cttcttctgc aactccacca aggtggaatg      840
cgatgaattc tatgcgaatt cgctcttcgt cgtcggcgag tttggtggca acgactacaa      900
tgcgccgctg tttgcgggga agggccttga ggaggcctac aagttcatgc cggatgtcat      960
ccaggctatc tccgatggca tcgagcaatt gattgctgag ggcgcaaggg agctgattgt     1020
acccggtgtg atgcccactg gatgcttccc tgtctacttg aacatgctcg atgagccggc     1080
cgatgggtat ggcccccaga gcggctgcgt ccgtcggtac aacacattct catgggtgca     1140
caatgcacat ctcaagcgca tgcttgagaa gctccggccc aagcacccca atgtgaggat     1200
catatatggc gattactaca cgcctgttat ccagttcatg cttcagcccg agaagtttgg     1260
attttacaag cagctaccta gggcatgctg cggggctcct gggtccgttg cgaaggccgc     1320
ttacaacttc aatgtcacag ccaaatgtgg tgaggctggc gcaaccgcgt gtgatgatcc     1380
atcaacccat tggagctggg atggcattca cctgacagag gcggcttacg gtcacattgc     1440
cagaggttgg gtatatggtc ctttcgctga ccaaccgatc ttccaatctt catgagaaag     1500
tcacttcttc cgttgtaatt gtagaggtgt atcacgatag tgcactgaaa tggagcaggg     1560
aaagtagttc ttccatatgg ttccaaggtt gcatacatgt atattttcat tctattacat     1620
tcattgcagt caggtacaaa ggtggaatag ggctgtcaaa agcttgattt tgtttatttg     1680
tcaggcgaca taactatgaa aatgtaacag acacatgatt gtgtaaaaaa aaaaaaaaaa     1740
aaaaaaaaaa                                                            1750
```

<210> SEQ ID NO 8
<211> LENGTH: 382
<212> TYPE: PRT
<213> ORGANISM: Oryza sativa

<400> SEQUENCE: 8

```
Met Gly Ala Val Arg Gly Ile Leu Val Val Ala Val Val Leu Ala Val
  1               5                  10                  15

Ala Ala Ile Leu Ala Gly Ala Ala Glu Gly Lys Val Asn Gly Lys Ala
             20                  25                  30

Lys Gly Lys Tyr Arg Ala Leu Phe Asn Phe Gly Asp Ser Leu Ala Asp
         35                  40                  45

Ala Gly Asn Leu Leu Ala Asn Gly Val Asp Phe Arg Leu Ala Thr Ala
     50                  55                  60

Gln Leu Pro Tyr Gly Gln Thr Phe Pro Gly His Pro Thr Gly Arg Cys
 65                  70                  75                  80

Ser Asp Gly Arg Leu Val Val Asp His Leu Ala Asp Glu Phe Gly Leu
                 85                  90                  95

Pro Leu Leu Pro Pro Ser Lys Leu Lys Asn Ser Ser Phe Ala His Gly
            100                 105                 110

Ala Asn Phe Ala Ile Thr Gly Ala Thr Ala Leu Asp Thr Pro Tyr Phe
        115                 120                 125

Glu Ala Lys Gly Leu Gly Ala Val Val Trp Asn Ser Gly Ala Leu Leu
    130                 135                 140

Thr Gln Ile Gln Trp Phe Arg Asp Leu Lys Pro Phe Phe Cys Asn Ser
145                 150                 155                 160

Thr Lys Val Glu Cys Asp Glu Phe Tyr Ala Asn Ser Leu Phe Val Val
                165                 170                 175

Gly Glu Phe Gly Gly Asn Asp Tyr Asn Ala Pro Leu Phe Ala Gly Lys
            180                 185                 190

Gly Leu Glu Glu Ala Tyr Lys Phe Met Pro Asp Val Ile Gln Ala Ile
```

-continued

|  |  |  | 195 |  |  |  | 200 |  |  |  | 205 |  |
|---|---|---|---|---|---|---|---|---|---|---|---|---|

Ser Asp Gly Ile Glu Gln Leu Ile Ala Glu Gly Ala Arg Glu Leu Ile
    210                 215                 220

Val Pro Gly Val Met Pro Thr Gly Cys Phe Pro Val Tyr Leu Asn Met
225                 230                 235                 240

Leu Asp Glu Pro Ala Asp Gly Tyr Gly Pro Gln Ser Gly Cys Val Arg
            245                 250                 255

Arg Tyr Asn Thr Phe Ser Trp Val His Asn Ala His Leu Lys Arg Met
        260                 265                 270

Leu Glu Lys Leu Arg Pro Lys His Pro Asn Val Arg Ile Ile Tyr Gly
    275                 280                 285

Asp Tyr Tyr Thr Pro Val Ile Gln Phe Met Leu Gln Pro Glu Lys Phe
290                 295                 300

Gly Phe Tyr Lys Gln Leu Pro Arg Ala Cys Cys Gly Ala Pro Gly Ser
305                 310                 315                 320

Val Ala Lys Ala Ala Tyr Asn Phe Asn Val Thr Ala Lys Cys Gly Glu
            325                 330                 335

Ala Gly Ala Thr Ala Cys Asp Asp Pro Ser Thr His Trp Ser Trp Asp
        340                 345                 350

Gly Ile His Leu Thr Glu Ala Tyr Gly His Ile Ala Arg Gly Trp
    355                 360                 365

Val Tyr Gly Pro Phe Ala Asp Gln Pro Ile Phe Gln Ser Ser
370                 375                 380

<210> SEQ ID NO 9
<211> LENGTH: 1432
<212> TYPE: DNA
<213> ORGANISM: Oryza sativa

<400> SEQUENCE: 9

```
gttctaacct ctgttttaat ttctttgcaa tgatggggag gcagagctcg tcggcggcga      60
ggagggtggt ggtggtggtg tgcgcggcga tggtggtggc ggcggcggcg cgcagaagt     120
acaatgcggt gtacaacttc ggggactcga tcacggacac cggcaacctg tgcaccaatg    180
gcaggccgtc gcagatcacc ttcacccagc ctccctacgg cgagacctac ttcggctccc    240
ctacctgccg ctgctgcgac ggccgcgtcg tcgtcgactt cctcgcgagt aagttcgggc    300
tgccgttcct gccgccgtcg aagtcgacga gcgccgactt caagaaggga gcgaacatgg    360
cgatcaccgg agccaccgcc atggacgcca acttcttccg ctccctcggc ctctccgaca    420
agatctggaa caacggcccc atcagctttc aaatccagtg gttccagcaa atctcctcct    480
ccgtctgcgg ccagaattgc aagagctacc tggcgaactc gctgttcgtg ttcggggagt    540
tcggcggcaa cgactacaat gcgatgctgt cggagggta cagcgcggac caggcgagca    600
cgtacacgtc gcagatcgtg gacaccatct ccaacggcgt cgagaagctc atcgccatgg    660
gcgccgtcga cgtcgtcgtc cccggcgtgc tccccatcgg ctgcttcccc atctacctca    720
ccatctacgg cacctcctcc agctccgact acgacagcct cggctgcctc aagaagttca    780
acgacctctc caccaaccac aacaatcagc tcaagaccaa gatctccgcg ctccaatcca    840
agtacaagtc cgcccgcatc atgtacgccg acttctactc cggcgtctac gacatggtcc    900
gcaaccccgg caactacgga tttagcacgg tgttcgagac gtgctgcggg tcaggcggcg    960
gcaagttcaa ctacaacaac aacgcgaggt gtgggatgtc aggcgcatca gcgtgctcca   1020
acccggcgtc gcatcttagc tgggacggca tccacctcac cgaggcagct acaagcaga   1080
```

-continued

```
tcactgacgg ctggctcaac ggcccgtact gtagcccggc catcctccac agctaaggca    1140
aaatgactgg aaagaacgag ccattagtta atttattact ttattattaa ggctggtgtt    1200
tattaattaa gcgggaatta attaaagggg aattgtttgg gttcttgatt tttatttggg    1260
tggcatatat ggtgggtggt gtgacggtga aatggtttac ttgcgttgcc aaaaaagcaa    1320
agaaagcgat ggcatctgta gaataaatgt tggttactgt tgtaatttga taattgtttc    1380
tcttccagaa tcaaatgaat catcaatggt attatactca aaaaaaaaaa aa            1432
```

<210> SEQ ID NO 10
<211> LENGTH: 368
<212> TYPE: PRT
<213> ORGANISM: Oryza sativa

<400> SEQUENCE: 10

```
Met Met Gly Arg Gln Ser Ser Ala Ala Arg Arg Val Val Val
  1               5                  10                  15

Val Cys Ala Ala Met Val Val Ala Ala Ala Ala Gln Lys Tyr Asn
             20                  25                  30

Ala Val Tyr Asn Phe Gly Asp Ser Ile Thr Asp Thr Gly Asn Leu Cys
         35                  40                  45

Thr Asn Gly Arg Pro Ser Gln Ile Thr Phe Thr Gln Pro Pro Tyr Gly
     50                  55                  60

Glu Thr Tyr Phe Gly Ser Pro Thr Cys Arg Cys Cys Asp Gly Arg Val
 65                  70                  75                  80

Val Val Asp Phe Leu Ala Ser Lys Phe Gly Leu Pro Phe Leu Pro Pro
                 85                  90                  95

Ser Lys Ser Thr Ser Ala Asp Phe Lys Lys Gly Ala Asn Met Ala Ile
            100                 105                 110

Thr Gly Ala Thr Ala Met Asp Ala Asn Phe Phe Arg Ser Leu Gly Leu
        115                 120                 125

Ser Asp Lys Ile Trp Asn Asn Gly Pro Ile Ser Phe Gln Ile Gln Trp
    130                 135                 140

Phe Gln Gln Ile Ser Ser Ser Val Cys Gly Gln Asn Cys Lys Ser Tyr
145                 150                 155                 160

Leu Ala Asn Ser Leu Phe Val Phe Gly Glu Phe Gly Gly Asn Asp Tyr
                165                 170                 175

Asn Ala Met Leu Phe Gly Gly Tyr Ser Ala Asp Gln Ala Ser Thr Tyr
            180                 185                 190

Thr Ser Gln Ile Val Asp Thr Ile Ser Asn Gly Val Glu Lys Leu Ile
        195                 200                 205

Ala Met Gly Ala Val Asp Val Val Pro Gly Val Leu Pro Ile Gly
    210                 215                 220

Cys Phe Pro Ile Tyr Leu Thr Ile Tyr Gly Thr Ser Ser Ser Ser Asp
225                 230                 235                 240

Tyr Asp Ser Leu Gly Cys Leu Lys Lys Phe Asn Asp Leu Ser Thr Asn
                245                 250                 255

His Asn Asn Gln Leu Lys Thr Lys Ile Ser Ala Leu Gln Ser Lys Tyr
            260                 265                 270

Lys Ser Ala Arg Ile Met Tyr Ala Asp Phe Tyr Ser Gly Val Tyr Asp
        275                 280                 285

Met Val Arg Asn Pro Gly Asn Tyr Gly Phe Ser Thr Val Phe Glu Thr
    290                 295                 300

Cys Cys Gly Ser Gly Gly Gly Lys Phe Asn Tyr Asn Asn Ala Arg
305                 310                 315                 320
```

```
Cys Gly Met Ser Gly Ala Ser Ala Cys Ser Asn Pro Ala Ser His Leu
            325                 330                 335

Ser Trp Asp Gly Ile His Leu Thr Glu Ala Ala Tyr Lys Gln Ile Thr
        340                 345                 350

Asp Gly Trp Leu Asn Gly Pro Tyr Cys Ser Pro Ala Ile Leu His Ser
        355                 360                 365

<210> SEQ ID NO 11
<211> LENGTH: 484
<212> TYPE: DNA
<213> ORGANISM: Glycine max
<220> FEATURE:
<221> NAME/KEY: unsure
<222> LOCATION: (234)
<223> OTHER INFORMATION: n = a, c, g or t
<220> FEATURE:
<221> NAME/KEY: unsure
<222> LOCATION: (348)
<223> OTHER INFORMATION: n = a, c, g or t

<400> SEQUENCE: 11
taccatttga aaatggcttc ttgtgtgtca tccatgtctt ctaccatcct catcctaatt      60
gccatctgca cactgtcctc acttctgtca gctgcatctg cagcaacaga ggagggacga    120
acaaggccct tcaaaagggt ctatgccttt ggagactctt tcacagacac tggcaacacc    180
aaaaatgccg aagtccaagt ggctttggt catgtttcaa actctcccta cggnaccact     240
ttcttcaacc actccacaaa caggtactca gatggtaggc ttgtgattga ttttgtagct    300
gaagcacttt cactgcctta cttgcccccc taccgtcaca gcaaaggnaa tgacactttt    360
ggggttaact ttgctgttgc tggctccaca accataaacc atttgttctt tgtgaagcac    420
aacctctccc ttgatatcac tgctcagtcc atccaaaccc aaatgatatg ggtcaacaag    480
tacc                                                                484

<210> SEQ ID NO 12
<211> LENGTH: 157
<212> TYPE: PRT
<213> ORGANISM: Glycine max

<400> SEQUENCE: 12

Met Ala Ser Cys Val Ser Ser Met Ser Ser Thr Ile Leu Ile Leu Ile
  1               5                  10                  15

Ala Ile Cys Thr Leu Ser Ser Leu Leu Ser Ala Ala Ser Ala Ala Thr
             20                  25                  30

Glu Glu Gly Arg Thr Arg Pro Phe Lys Arg Val Tyr Ala Phe Gly Asp
        35                  40                  45

Ser Phe Thr Asp Thr Gly Asn Thr Lys Asn Ala Glu Gly Pro Ser Gly
     50                  55                  60

Phe Gly His Val Ser Asn Ser Pro Tyr Gly Thr Thr Phe Asn His
 65                  70                  75                  80

Ser Thr Asn Arg Tyr Ser Asp Gly Arg Leu Val Ile Asp Phe Val Ala
             85                  90                  95

Glu Ala Leu Ser Leu Pro Tyr Leu Pro Pro Tyr Arg His Ser Lys Gly
            100                 105                 110

Asn Asp Thr Phe Gly Val Asn Phe Ala Val Ala Gly Ser Thr Ala Ile
        115                 120                 125

Asn His Leu Phe Phe Val Lys His Asn Leu Ser Leu Asp Ile Thr Ala
    130                 135                 140
```

Gln Ser Ile Gln Thr Gln Met Ile Trp Phe Asn Arg Tyr
145                 150                 155

<210> SEQ ID NO 13
<211> LENGTH: 1662
<212> TYPE: DNA
<213> ORGANISM: Glycine max

<400> SEQUENCE: 13

```
gcacgaggtt tgattgtcct agctttgagc aacatcatga agatctccat tctctttatc     60
acaatctttt cttgtggttt tcttggaaat gttgtttcaa atgctagtcc tcttccatat    120
gaagctattt ttaactttgg tgactctata agtgatactg gaaatgctgc tcataaccac    180
ccacctatgc ctggcaatag tccttatggt tcaacatact ttaaacatcc ttctggacgt    240
atgtcaaatg gacgactaat catagatttt atagccgagg catatgggat gccaatgttg    300
ccagcctatt tgaatctcac caaaggacaa gacattaaga aggagtgaa ttttgcatac    360
gctggttcaa ctgcacttga taaggatttt ttagtacaaa aagaatcaa tatagaggaa    420
gctacttttt cattgagtgc tcaatttgat tggtttaaag gactcaaatc ctcccttgt    480
acaagcaaag aagagtgcga taattacttc aaaaactcat tgtttctagt aggagagatt    540
ggtgggaatg acatcaatgc actcatccca tataaaaata ttacagaact tcgagaaatg    600
gttccatcaa ttgttgaaac aattgccaat accacctcta aattaataga agaaggagcg    660
gtagaactag tggtaccagg gaacttccca attgggtgta attctgctgt tttggcaata    720
gtgaatagcg aaaagaaaga agactatgat caatttgggt gtttgatagc ttacaatact    780
ttcattgagt actacaatga gcaactcaaa aaggctatag agacattaag aaaaaacaac    840
gcacatgtta agataacata ttttgattac tatggtgcta ccaaacgttt atttcaagca    900
ccacaacaat atggcttttc ttccggtaag actgaaactt tcagagcatg ttgtggaaag    960
ggtgaacctt acaatctcag ttttcaaata ttatgtggta gtcctgctgc aatagtttgc   1020
tcagatcctt caaaacaaat aaattgggat gggcctcatt ttactgaagc agcgtatagg   1080
ctaatagcta agggactagt tgagggccct ttcgctaatc catctctcaa atcccctcct   1140
ttcaagatag cttagaattt aagcatggat gaaaatgaac aagaataagc ttttctccat   1200
atgtttcatg tgtatatttg taacatggat gacataagca aagtgttgct aaaacaaaca   1260
tcttgtattc catgatggac aatatattat taactattgt gtaaaaaaaa aaaaaaaaa    1320
aaaaaaaaa aaaaaaaaa aaaaaaaaa aaaaaaaaa aaaaaaaaa aaaaaaaaa         1380
aaaaaaaaa accccggggg gggggccggg aaccaaattc ccccaaaaag gatccttta     1440
accccccccca aagggccttt ttttaaaaac tccggaaggg gaaaaacccg gggttaacca   1500
aattaaaccc ctttaaaaaa aacccccttt tccaaagggg ggtaaaaaaa aaaagccccc   1560
ccacctttcc cccttccaaa aatttcccca ccctaaatgg aaaagggaac cccccctta    1620
ggggccaaaa aaaccggggg ggtggttggt ttaaccccaa at                      1662
```

<210> SEQ ID NO 14
<211> LENGTH: 372
<212> TYPE: PRT
<213> ORGANISM: Glycine max

<400> SEQUENCE: 14

Met Lys Ile Ser Ile Leu Phe Ile Thr Ile Phe Ser Cys Gly Phe Leu
1               5                   10                  15

Gly Asn Val Val Ser Asn Ala Ser Pro Leu Pro Tyr Glu Ala Ile Phe

```
                20                  25                  30
Asn Phe Gly Asp Ser Ile Ser Asp Thr Gly Asn Ala Ala His Asn His
             35                  40                  45
Pro Pro Met Pro Gly Asn Ser Pro Tyr Gly Ser Thr Tyr Phe Lys His
 50                  55                  60
Pro Ser Gly Arg Met Ser Asn Gly Arg Leu Ile Ile Asp Phe Ile Ala
 65                  70                  75                  80
Glu Ala Tyr Gly Met Pro Met Leu Pro Ala Tyr Leu Asn Leu Thr Lys
                 85                  90                  95
Gly Gln Asp Ile Lys Lys Gly Val Asn Phe Ala Tyr Ala Gly Ser Thr
                100                 105                 110
Ala Leu Asp Lys Asp Phe Leu Val Gln Lys Arg Ile Asn Ile Glu Glu
            115                 120                 125
Ala Thr Phe Ser Leu Ser Ala Gln Phe Asp Trp Phe Lys Gly Leu Lys
        130                 135                 140
Ser Ser Leu Cys Thr Ser Lys Glu Glu Cys Asp Asn Tyr Phe Lys Asn
145                 150                 155                 160
Ser Leu Phe Leu Val Gly Glu Ile Gly Gly Asn Asp Ile Asn Ala Leu
                165                 170                 175
Ile Pro Tyr Lys Asn Ile Thr Glu Leu Arg Glu Met Val Pro Ser Ile
            180                 185                 190
Val Glu Thr Ile Ala Asn Thr Thr Ser Lys Leu Ile Glu Glu Gly Ala
        195                 200                 205
Val Glu Leu Val Val Pro Gly Asn Phe Pro Ile Gly Cys Asn Ser Ala
    210                 215                 220
Val Leu Ala Ile Val Asn Ser Glu Lys Lys Glu Asp Tyr Asp Gln Phe
225                 230                 235                 240
Gly Cys Leu Ile Ala Tyr Asn Thr Phe Ile Glu Tyr Tyr Asn Glu Gln
                245                 250                 255
Leu Lys Lys Ala Ile Glu Thr Leu Arg Lys Asn Asn Ala His Val Lys
            260                 265                 270
Ile Thr Tyr Phe Asp Tyr Tyr Gly Ala Thr Lys Arg Leu Phe Gln Ala
        275                 280                 285
Pro Gln Gln Tyr Gly Phe Ser Ser Gly Lys Thr Glu Thr Phe Arg Ala
    290                 295                 300
Cys Cys Gly Lys Gly Glu Pro Tyr Asn Leu Ser Phe Gln Ile Leu Cys
305                 310                 315                 320
Gly Ser Pro Ala Ala Ile Val Cys Ser Asp Pro Ser Lys Gln Ile Asn
                325                 330                 335
Trp Asp Gly Pro His Phe Thr Glu Ala Ala Tyr Arg Leu Ile Ala Lys
            340                 345                 350
Gly Leu Val Glu Gly Pro Phe Ala Asn Pro Ser Leu Lys Ser Pro Pro
        355                 360                 365
Phe Lys Ile Ala
    370

<210> SEQ ID NO 15
<211> LENGTH: 1405
<212> TYPE: DNA
<213> ORGANISM: Glycine max

<400> SEQUENCE: 15
gcacgagatt gaacagcgga acatacgatg atcacccgcc accatgcctt tgtccgctaa    60
aattagttcg ctgcaacgac aaatacaaag gttgcgtatc gtgctagtgc tactactact   120
```

-continued

```
acttgctgct actgtcactg cttgctacac ctcactcttc agcttcggag attccctcac    180
tgataccggc aacttgtact tcatttcccc tcgtcagagc cccgattgct tgctccctcc    240
ctacggacaa acccattttc atcgcccaa tggacgatgc tccgatggac gccttatcct    300
cgatttcctc gccgagtctc tgggcttcc gtatgtgaaa ccgtatctgg gtttcaagaa    360
cggcgcggtg aaacgcggga atattgagca gggagtgaat tttgcggtgg ccggagccac    420
ggcgctggac cgcggtttct ttgaagaaaa ggggttcgct gttgatgtga ccgcaaactt    480
ttctctgggg gttcagttag attggttcaa ggaattgctg ccttctctct gcaattcttc    540
ttcaagctgc aaaaaagtta ttggcagctc cttatttatt gtgggagaga ttggaggcaa    600
tgattatggc tatcctttgt ctgaaacaac cgcatttgga gatcttgtga cttacatacc    660
ccaagtaata tctgtaatca cttcagcaat cagggaattg attgatttag ggctgtaac    720
gtttatggtt cctggaagtt taccacttgg atgcaatcca gcctatttaa caattttgc    780
gactatagat aaagaggagt atgaccaagc tggctgtttg aaatggttaa atacgttcta    840
tgaataccac aatgagctgc tccagattga aataaatcgg cttcgagtgc tatatcctct    900
taccaatatc atttatgcag attatttcaa cgctgcattg gagttttaca attctccaga    960
acaatttggg tttggtggaa atgttctcaa gtttgttgt ggaggtgggg gtccttacaa   1020
ttacaatgaa acggccatgt gtggggacgc aggagtggtt gcttgtgatg atccttcaca   1080
atatgttagc tgggatggct atcatttgac cgaggctgct tatagatgga tgaccaaagg   1140
tttattagat gggccataca caattcctaa atttaatgtc tcgtgtttca taggtgaaac   1200
catcagagat tttaataact atgcaatgaa atataaatca atgtaaaata tccacgtatt   1260
tgatgaggtt taagtagtac tccaataagg tgattttcac tgcctcgtgc agttgtatct   1320
gtttaatgaa tgtaataatgc ataacgtttt ttagcagcaa aaaaaaaaa aaaaaaaaa   1380
aaaaaaaaa aaaaaaaaa aaaaa                                         1405
```

<210> SEQ ID NO 16
<211> LENGTH: 400
<212> TYPE: PRT
<213> ORGANISM: Glycine max

<400> SEQUENCE: 16

```
Met Pro Leu Ser Ala Lys Ile Ser Ser Leu Gln Arg Gln Ile Gln Arg
  1               5                  10                  15

Leu Arg Ile Val Leu Val Leu Leu Leu Ala Ala Thr Val Thr
             20                  25                  30

Ala Cys Tyr Thr Ser Leu Phe Ser Phe Gly Asp Ser Leu Thr Asp Thr
         35                  40                  45

Gly Asn Leu Tyr Phe Ile Ser Pro Arg Gln Ser Pro Asp Cys Leu Leu
     50                  55                  60

Pro Pro Tyr Gly Gln Thr His Phe His Arg Pro Asn Gly Arg Cys Ser
 65                  70                  75                  80

Asp Gly Arg Leu Ile Leu Asp Phe Leu Ala Glu Ser Leu Gly Leu Pro
                 85                  90                  95

Tyr Val Lys Pro Tyr Leu Gly Phe Lys Asn Gly Ala Val Lys Arg Gly
            100                 105                 110

Asn Ile Glu Gln Gly Val Asn Phe Ala Val Ala Gly Ala Thr Ala Leu
        115                 120                 125

Asp Arg Gly Phe Phe Glu Glu Lys Gly Phe Ala Val Asp Val Thr Ala
    130                 135                 140
```

-continued

```
Asn Phe Ser Leu Gly Val Gln Leu Asp Trp Phe Lys Glu Leu Leu Pro
145                 150                 155                 160

Ser Leu Cys Asn Ser Ser Ser Cys Lys Lys Val Ile Gly Ser Ser
            165                 170                 175

Leu Phe Ile Val Gly Glu Ile Gly Asn Asp Tyr Gly Tyr Pro Leu
            180                 185                 190

Ser Glu Thr Thr Ala Phe Gly Asp Leu Val Thr Tyr Ile Pro Gln Val
        195                 200                 205

Ile Ser Val Ile Thr Ser Ala Ile Arg Glu Leu Ile Asp Leu Gly Ala
        210                 215                 220

Val Thr Phe Met Val Pro Gly Ser Leu Pro Leu Gly Cys Asn Pro Ala
225                 230                 235                 240

Tyr Leu Thr Ile Phe Ala Thr Ile Asp Lys Glu Glu Tyr Asp Gln Ala
                245                 250                 255

Gly Cys Leu Lys Trp Leu Asn Thr Phe Tyr Glu Tyr His Asn Glu Leu
                260                 265                 270

Leu Gln Ile Glu Ile Asn Arg Leu Arg Val Leu Tyr Pro Leu Thr Asn
        275                 280                 285

Ile Ile Tyr Ala Asp Tyr Phe Asn Ala Ala Leu Glu Phe Tyr Asn Ser
290                 295                 300

Pro Glu Gln Phe Gly Phe Gly Gly Asn Val Leu Lys Val Cys Cys Gly
305                 310                 315                 320

Gly Gly Gly Pro Tyr Asn Tyr Asn Glu Thr Ala Met Cys Gly Asp Ala
                325                 330                 335

Gly Val Val Ala Cys Asp Asp Pro Ser Gln Tyr Val Ser Trp Asp Gly
                340                 345                 350

Tyr His Leu Thr Glu Ala Ala Tyr Arg Trp Met Thr Lys Gly Leu Leu
        355                 360                 365

Asp Gly Pro Tyr Thr Ile Pro Lys Phe Asn Val Ser Cys Phe Ile Gly
        370                 375                 380

Glu Thr Ile Arg Asp Phe Asn Asn Tyr Ala Met Lys Tyr Lys Ser Met
385                 390                 395                 400
```

```
<210> SEQ ID NO 17
<211> LENGTH: 726
<212> TYPE: DNA
<213> ORGANISM: Triticum aestivum
<220> FEATURE:
<221> NAME/KEY: unsure
<222> LOCATION: (224)..(225)
<223> OTHER INFORMATION: n = a, c, g or t
<220> FEATURE:
<221> NAME/KEY: unsure
<222> LOCATION: (653)
<223> OTHER INFORMATION: n = a, c, g or t
<220> FEATURE:
<221> NAME/KEY: unsure
<222> LOCATION: (664)
<223> OTHER INFORMATION: n = a, c, g or t
<220> FEATURE:
<221> NAME/KEY: unsure
<222> LOCATION: (666)..(667)
<223> OTHER INFORMATION: n = a, c, g or t
<220> FEATURE:
<221> NAME/KEY: unsure
<222> LOCATION: (711)
<223> OTHER INFORMATION: n = a, c, g or t
<220> FEATURE:
<221> NAME/KEY: unsure
<222> LOCATION: (720)
<223> OTHER INFORMATION: n = a, c, g or t
```

-continued

```
<400> SEQUENCE: 17
ctgctccgct ctgctctctg ccccgcccgc cggctcatct ccgcgcgcag aggcagcgtc     60
gcagcgagca caccaccttc gacccctcct cctccccgta acctgccggc tcttcccgcc    120
gcctcgcttg cgagtgagac gatggcgagg ccgtcgtcgt cgccgatggc gacgaggctg    180
ccgctgttgc ttgtgctgct gtcgtcgctg gccctgcagg cggnnggcgc agaagtacaa    240
tgcggtgtac agcttcggcg actcgatcac ggacacgggc aacctgtgca ccaacggccg    300
ccctcggcg atcaccttca cgcagccgcc ctacggcgag acctacttcg ggagccccac     360
ctgccgctgc tccgacggcc gggtcatcgt cgacttcctc agcaccaagt acggcctccc    420
cttcctgccc cctccaagt ccacctccgc cgacttcaag aagggcgcca acatggccat     480
caccgggcgc caccgccatg gacgcccct tcttccgctc cctcgggctc tcgggacaag     540
attctgggaa caacgggcc atcaacttcc aactccaagt gggttccaag acatcaactc     600
ctccgttctg gcggcaacaa ctgcaaagag taccttgggc aactcgctct tancttccgg    660
ggantnnggg ggaacgatac aacgcgatgc tttcgggaac tacaacacgg ncaagcgaan    720
acgttt                                                                726

<210> SEQ ID NO 18
<211> LENGTH: 195
<212> TYPE: PRT
<213> ORGANISM: Triticum aestivum
<220> FEATURE:
<221> NAME/KEY: UNSURE
<222> LOCATION: (28)
<223> OTHER INFORMATION: Xaa = any amino acid
<220> FEATURE:
<221> NAME/KEY: UNSURE
<222> LOCATION: (171)
<223> OTHER INFORMATION: Xaa = any amino acid
<220> FEATURE:
<221> NAME/KEY: UNSURE
<222> LOCATION: (175)..(176)
<223> OTHER INFORMATION: Xaa = any amino acid
<220> FEATURE:
<221> NAME/KEY: UNSURE
<222> LOCATION: (193)
<223> OTHER INFORMATION: Xaa = any amino acid

<400> SEQUENCE: 18

Met Ala Arg Pro Ser Ser Pro Met Ala Thr Arg Leu Pro Leu Leu
 1               5                  10                  15

Leu Val Leu Leu Ser Ser Leu Ala Leu Gln Ala Xaa Gly Ala Glu Val
            20                  25                  30

Gln Cys Gly Val Gln Leu Arg Arg Leu Asp His Gly His Gly Gln Pro
        35                  40                  45

Val His Gln Arg Pro Pro Leu Gly Asp His Leu His Ala Ala Ala Leu
    50                  55                  60

Arg Arg Asp Leu Leu Arg Glu Pro His Leu Pro Leu Leu Arg Arg Pro
65                  70                  75                  80

Gly His Arg Arg Leu Pro Gln His Gln Val Arg Pro Pro Leu Pro Ala
                85                  90                  95

Pro Leu Gln Val His Leu Arg Arg Leu Gln Glu Gly Arg Gln His Gly
            100                 105                 110

His His Arg Ala Pro Pro Pro Trp Thr Pro Pro Ser Ser Ala Pro Ser
        115                 120                 125

Gly Ser Arg Asp Lys Ile Leu Gly Thr Thr Gly Pro Ser Thr Ser Asn
    130                 135                 140
```

-continued

```
Ser Lys Trp Val Pro Arg His Gln Leu Leu Arg Ser Gly Gly Asn Asn
145                 150                 155                 160

Cys Lys Glu Tyr Leu Gly Gln Leu Ala Leu Xaa Phe Arg Gly Xaa Xaa
                165                 170                 175

Gly Asn Asp Thr Thr Arg Cys Phe Arg Glu Leu Gln His Gly Gln Ala
            180                 185                 190

Xaa Thr Phe
    195
```

<210> SEQ ID NO 19
<211> LENGTH: 784
<212> TYPE: DNA
<213> ORGANISM: Triticum aestivum
<220> FEATURE:
<221> NAME/KEY: unsure
<222> LOCATION: (706)
<223> OTHER INFORMATION: n = a, c, g or t
<220> FEATURE:
<221> NAME/KEY: unsure
<222> LOCATION: (779)
<223> OTHER INFORMATION: n = a, c, g or t

<400> SEQUENCE: 19

```
gttcatgccg ggatgtcatc caggcatct ccgatggcgt cgaggaattg atcgccgagg      60
gggcagtgga tctcatcgtg ccagggtga tgcccactgg gtgcttcccc gtgtacctga    120
acatgctcga catgccagcc acgagtatg gcgcccggag cgggtgcatc cgtcagtaca    180
acaccttctc atgggtgcac aatgcacacc tcaagagagc actcgagaag ctccggccca    240
agcaccccaa tgtgcggatc atatatggcg actactacac gccagttgtc agttcatgc    300
tccagcctga gaagtttgga ttctacaagc agttacctag gcatgctgtg ggggctcctg    360
ggtccgttgc aaagccgcta caacttcacg tgacagccaa atgcggggag cctggtgcca    420
ctgcctgtgc tgacccaacg acccactgga gctgggacgg tattcacttg acggaggctg    480
cttatggtca tatcgccagg ggttggctat atggcccttt cgcagaccaa ccgattgttc    540
agtcctcgtg agcattccac ctctgctgtt gcacctgtag agcgtctgag aatagcacac    600
taaactggag aagggaaagt agttcttcca tatagtccca atggttcata cctgtatatt    660
ttcatttgat tgaattcatt gcaagtgggg tacaaaggtg aaatangga taccaaaagc    720
atgatttgtt ttatctgtga gtggtataaa tgtaaaatgt aatgaacaca tgattacant    780
aaaa                                                                 784
```

<210> SEQ ID NO 20
<211> LENGTH: 182
<212> TYPE: PRT
<213> ORGANISM: Triticum aestivum

<400> SEQUENCE: 20

```
Ser Cys Arg Asp Val Ile Gln Gly Ile Ser Asp Gly Val Glu Glu Leu
1               5                   10                  15

Ile Ala Glu Gly Ala Val Asp Leu Ile Val Pro Gly Val Met Pro Thr
                20                  25                  30

Gly Cys Phe Pro Val Tyr Leu Asn Met Leu Asp Met Pro Ala His Glu
            35                  40                  45

Tyr Gly Ala Arg Ser Gly Cys Ile Arg Gln Tyr Asn Thr Phe Ser Trp
        50                  55                  60

Val His Asn Ala His Leu Lys Arg Ala Leu Glu Lys Leu Arg Pro Lys
65                  70                  75                  80
```

```
His Pro Asn Val Arg Ile Ile Tyr Gly Asp Tyr Tyr Thr Pro Val Val
            85                  90                  95

Gln Phe Met Leu Gln Pro Glu Lys Phe Gly Phe Tyr Lys Gln Leu Pro
            100                 105                 110

Arg Ala Cys Cys Gly Ala Pro Gly Ser Val Ala Lys Pro Leu Gln Leu
            115                 120                 125

His Val Thr Ala Lys Cys Gly Glu Pro Gly Ala Thr Ala Cys Ala Asp
        130                 135                 140

Pro Thr Thr His Trp Ser Trp Asp Gly Ile His Leu Thr Glu Ala Ala
145                 150                 155                 160

Tyr Gly His Ile Ala Arg Gly Trp Leu Tyr Gly Pro Phe Ala Asp Gln
            165                 170                 175

Pro Ile Val Gln Ser Ser
            180

<210> SEQ ID NO 21
<211> LENGTH: 1725
<212> TYPE: DNA
<213> ORGANISM: Zea mays

<400> SEQUENCE: 21
ccacgcgtcc ggagtgaacc acgccaccac acgcagcgag cgagcgccca aagaaacgcc      60
gtagcagcca ccaccaccac caacccctto ctccctttcc ctctccgccg cccgcctctc     120
tacaagaacc ctcacccgac cgccgataac tacctagctc ccacctcgct cctcgactcc     180
gtcttctcta ttcttccatt tagcggagat cctagaacct aggggcagcc agccaggggg     240
aacgggccgc gatgggagga aggggcgcga tgctcgctgt ggtgttggtg gttcttgcgg     300
cggttggcgc cgcggcggaa tcgatggagg cggcagccaa ggggaggtac cacgcgctct     360
tcaactttgg ggactcgcta ccgacgctg caacctcat ccagaacggc accccggaga     420
tcctggccac cgcgcgcctg ccctacggcc agacctactt cggaaagccc accggccgct     480
gctccgatgg acgtctcgtc atcgaccacc tcgcgcaaga gttcggcctg ccgctgctgc     540
cgccgtccaa ggccaagaac gccagcttcg cgcacggcgc caacttcgcc atcaccggcg     600
ccaccgcgct cgacacgccc tacttcgagg ccaaggggct cggtgccgtc atctggaact     660
ccggagcgct catgacccaa atccagtggt tccgtgatct caagcctttc ttctgcaaca     720
ccacggaggc atgcaagaaa ttcttttgcga aggcgctgtt tgtggtgggt gagtttggag     780
gcaacgacta caatgctccc ctcttttgcgg gcatgggcat ccctgaggcc tacaaattca     840
tgcccgatgt catacagggc atctctgacg gtattgaggc actgattgct gagggggctg     900
ttgagatgat tgtgcctggt gtcatgccca cgggctgctt cccagtttac ttgaacatgc     960
ttgatgagcc caaagaagga tacggccccc acagtggttg tgtccgccgg tacaacacat    1020
tctcctgggt gcacaatgca catcttaagg ccatgcttga aagctccgg ctaagcacc     1080 ccaatgtgag gatcatatat ggcgattact acactccagt cgtccagttc atgcttcagc    1140
ctgagaagtt tggttttgcc agacaactgc ccagggcatg ttgtggggcg ccatcgactc    1200
ctgagagagc agcttacaac ttcaatgtca cggccaaatg cggtgagcct ggtgcaactg    1260
cctgtgctga tccgacaacc cattggagct gggacggcat tcacctgacg gaggctgcct    1320
accgccatat cgccaaggc tggctatacg gccttttcgc ggaccaaccg atcatccaat    1380
cctcatgatc atgccgttcc tgcggtagag tttatcaaag tagcattgag agtgagagaa    1440
aaaaaatgga gcggggaaag taggtcttcc atacagttcc aatgcttgca tacttgtaca    1500
```

```
tctccatttg attgtattca tttgccatgg gggtacaaag gtgggatagt aggtcgcaca      1560
aaggcctgat tcttgattt gtcaggttgg ggggtataaa tatgaaagtt gttacgcaca      1620
gataatcatg tatattgtgt ccaaaaaaaa aaaaaaaaaa aaaaaaaaaa aaaaaaaaaa     1680
aaaaaaaaaa aaaaaaaaaa aaaaaaaaaa aaaaaaaaaa aaaaa                     1725
```

<210> SEQ ID NO 22
<211> LENGTH: 378
<212> TYPE: PRT
<213> ORGANISM: Zea mays

<400> SEQUENCE: 22

```
Met Gly Gly Arg Gly Ala Met Leu Ala Val Val Leu Val Val Leu Ala
 1               5                  10                  15

Ala Val Gly Ala Ala Ala Glu Ser Met Glu Ala Ala Ala Lys Gly Arg
                20                  25                  30

Tyr His Ala Leu Phe Asn Phe Gly Asp Ser Leu Ala Asp Ala Gly Asn
            35                  40                  45

Leu Ile Gln Asn Gly Thr Pro Glu Ile Leu Ala Thr Ala Arg Leu Pro
        50                  55                  60

Tyr Gly Gln Thr Tyr Phe Gly Lys Pro Thr Gly Arg Cys Ser Asp Gly
 65                  70                  75                  80

Arg Leu Val Ile Asp His Leu Ala Gln Glu Phe Gly Leu Pro Leu Leu
                 85                  90                  95

Pro Pro Ser Lys Ala Lys Asn Ala Ser Phe Ala His Gly Ala Asn Phe
            100                 105                 110

Ala Ile Thr Gly Ala Thr Ala Leu Asp Thr Pro Tyr Phe Glu Ala Lys
        115                 120                 125

Gly Leu Gly Ala Val Ile Trp Asn Ser Gly Ala Leu Met Thr Gln Ile
    130                 135                 140

Gln Trp Phe Arg Asp Leu Lys Pro Phe Phe Cys Asn Thr Thr Glu Ala
145                 150                 155                 160

Cys Lys Lys Phe Ala Lys Ala Leu Phe Val Val Gly Glu Phe Gly
                165                 170                 175

Gly Asn Asp Tyr Asn Ala Pro Leu Phe Ala Gly Met Gly Ile Pro Glu
            180                 185                 190

Ala Tyr Lys Phe Met Pro Asp Val Ile Gln Gly Ile Ser Asp Gly Ile
        195                 200                 205

Glu Ala Leu Ile Ala Glu Gly Ala Val Glu Met Ile Val Pro Gly Val
    210                 215                 220

Met Pro Thr Gly Cys Phe Pro Val Tyr Leu Asn Met Leu Asp Glu Pro
225                 230                 235                 240

Lys Glu Gly Tyr Gly Pro His Ser Gly Cys Val Arg Arg Tyr Asn Thr
                245                 250                 255

Phe Ser Trp Val His Asn Ala His Leu Lys Ala Met Leu Glu Lys Leu
            260                 265                 270

Arg Ala Lys His Pro Asn Val Arg Ile Ile Tyr Gly Asp Tyr Tyr Thr
        275                 280                 285

Pro Val Val Gln Phe Met Leu Gln Pro Glu Lys Phe Gly Phe Ala Arg
    290                 295                 300

Gln Leu Pro Arg Ala Cys Cys Gly Ala Pro Ser Thr Pro Glu Arg Ala
305                 310                 315                 320

Ala Tyr Asn Phe Asn Val Thr Ala Lys Cys Gly Glu Pro Gly Ala Thr
                325                 330                 335
```

```
Ala Cys Ala Asp Pro Thr Thr His Trp Ser Trp Asp Gly Ile His Leu
            340                 345                 350

Thr Glu Ala Ala Tyr Arg His Ile Ala Lys Gly Trp Leu Tyr Gly Pro
        355                 360                 365

Phe Ala Asp Gln Pro Ile Ile Gln Ser Ser
    370                 375
```

<210> SEQ ID NO 23
<211> LENGTH: 1211
<212> TYPE: DNA
<213> ORGANISM: Zea mays

<400> SEQUENCE: 23

```
ccacgcgtcc gctagcaata cttgaagatg aacaaccata tttccattct agtgattctc    60
atcgtcgatg tgtctgttgt cctcctgctc aattcccatg tagggttatg cagctgctac   120
aaccgcatct ttagttttgg tgacgatacc atggacactg gaaatttcat tcacttgatt   180
gggaaggccc catctaagta caaggaagcc ccctatggca agacattttt tagacatgca   240
actggccgca tttctgatgg tcgtgtcctc attgatttct atgcggaagc actaaaactg   300
ccaatgatac cacccatttt acctgagaag aactttgggt gtttcccaca tggcgccaac   360
ttcgctgtgt tggtgccac ggcacgtggc aaagtcttct tttcagggag ccctggtgt    420
ataggcacac aaatgtactg gtttgatcaa ttggtagatc gtatagctcc cggagatgct   480
gccaagaagc aatttctaag tgattctctt gtcattatgg gtggaattgg tcaaaatgac   540
tactactcat atttcatcaa aggtaaacct cccaaggatg gaaatatcat ttcagatgtc   600
atcgcagaca taagccattt catcgaggag cttattgtcg ttaatggggc gaaagcattc   660
gtggtcgcca taactttcc cgttgggtgt ttggcatcat acctaagtag gttccacagt   720
gacgaccatg aggactacga tgagcatggg tgccttaagt cgttcaatga gttctcccaa   780
aagcataatg agcaacttta ttctgccatc ggacaaatca gatactctta cccaaatgtg   840
aagtaatct atgctgacta ctacaacgcc accatggaat tcatcaagaa gcctagtaga   900
tttggtattg gtgatcctct agtagcatgt tgtggcggca atggaccata ccacaccagc  960
atggagtgca atggcacagc aaagctttgg ggtgacccac accacttcgc caattgggat  1020
ggcatgcaca tgacagagaa ggcatacaac atcattatgg aagggtgtt aaatgggcca  1080
tttgctgatc ctccatttcc acttagttgc taggattagt tacgctagga attccttaca  1140
acatgtagcc aatatttttt ataataatgg aagtattttg gatttatact aaaaaaaaaa  1200
aaaaaaaaa g                                                        1211
```

<210> SEQ ID NO 24
<211> LENGTH: 361
<212> TYPE: PRT
<213> ORGANISM: Zea mays

<400> SEQUENCE: 24

```
Met Asn Asn His Ile Ser Ile Leu Val Ile Leu Ile Val Asp Val Ser
  1               5                  10                  15

Val Val Leu Leu Leu Asn Ser His Val Gly Leu Cys Ser Cys Tyr Asn
             20                  25                  30

Arg Ile Phe Ser Phe Gly Asp Asp Thr Met Asp Thr Gly Asn Phe Ile
         35                  40                  45

His Leu Ile Gly Lys Ala Pro Ser Lys Tyr Lys Glu Ala Pro Tyr Gly
     50                  55                  60
```

Lys Thr Phe Phe Arg His Ala Thr Gly Arg Ile Ser Asp Gly Arg Val
65                  70                  75                  80

Leu Ile Asp Phe Tyr Ala Glu Ala Leu Lys Leu Pro Met Ile Pro Pro
            85                  90                  95

Ile Leu Pro Glu Lys Asn Phe Gly Cys Phe Pro His Gly Ala Asn Phe
        100                 105                 110

Ala Val Phe Gly Ala Thr Ala Arg Gly Lys Val Phe Phe Ser Gly Ser
    115                 120                 125

Pro Trp Cys Ile Gly Thr Gln Met Tyr Trp Phe Asp Gln Leu Val Asp
130                 135                 140

Arg Ile Ala Pro Gly Asp Ala Lys Lys Gln Phe Leu Ser Asp Ser
145                 150                 155                 160

Leu Val Ile Met Gly Gly Ile Gly Gln Asn Asp Tyr Tyr Ser Tyr Phe
                165                 170                 175

Ile Lys Gly Lys Pro Pro Lys Asp Gly Asn Ile Ile Ser Asp Val Ile
            180                 185                 190

Ala Asp Ile Ser His Phe Ile Glu Glu Leu Ile Val Val Asn Gly Ala
        195                 200                 205

Lys Ala Phe Val Val Ala Asn Asn Phe Pro Val Gly Cys Leu Ala Ser
    210                 215                 220

Tyr Leu Ser Arg Phe His Ser Asp Asp His Glu Asp Tyr Asp Glu His
225                 230                 235                 240

Gly Cys Leu Lys Ser Phe Asn Glu Phe Ser Gln Lys His Asn Glu Gln
                245                 250                 255

Leu Tyr Ser Ala Ile Gly Gln Ile Arg Tyr Ser Tyr Pro Asn Val Lys
            260                 265                 270

Val Ile Tyr Ala Asp Tyr Tyr Asn Ala Thr Met Glu Phe Ile Lys Lys
        275                 280                 285

Pro Ser Arg Phe Gly Ile Gly Asp Pro Leu Val Ala Cys Cys Gly Gly
    290                 295                 300

Asn Gly Pro Tyr His Thr Ser Met Glu Cys Asn Gly Thr Ala Lys Leu
305                 310                 315                 320

Trp Gly Asp Pro His His Phe Ala Asn Trp Asp Gly Met His Met Thr
                325                 330                 335

Glu Lys Ala Tyr Asn Ile Ile Met Glu Gly Val Leu Asn Gly Pro Phe
            340                 345                 350

Ala Asp Pro Pro Phe Pro Leu Ser Cys
        355                 360

<210> SEQ ID NO 25
<211> LENGTH: 1439
<212> TYPE: DNA
<213> ORGANISM: Glycine max

<400> SEQUENCE: 25
gcacgagtac catttgaaaa tggcttcttg tgtgtcatcc atgtcttcta ccatcctcat      60
cctaattgcc atctgcacac tgtcctcact tctgtcagct gcatctgcag caacagagga    120
gggacgaaca aggcccttca aagggtctat gcctttggga gactctttca cagacactgg    180
caacaccaaa aatgccgaag gtccaagtgg ctttggtcat gtttcaaact ctccctacgg    240
caccactttc ttcaaccact ccacaaacag gtactcagat ggtaggcttg tgattgattt    300
tgtagctgaa gcacttttca ctgccttactt gccccctac cgtcacagca aaggcaatga    360
cactttggt gttaactttg ctgttgctgg ctccacagcc ataaaccatt tgttctttgt    420

-continued

```
gaagcacaac ctctcccttg atatcactgc tcagtccatc caaacccaga tgatatggtt        480
caacaggtac ctagagagcc aggaatgtca agaatcaaag tgtaatgatt ttgatgacac        540
tctgttttgg tttggggaga ttggagtcaa tgactatgcc tacactcttg gatctactgt        600
ctcagatgag accataagga agcttgcaat cagcagtgtc tcaggagctt tacagacgtt        660
gcttgagaag ggtgccaagt acctagttgt gcagggtatg cctctaactg ggtgcttgac        720
attgtccatg tacctggctc ctccagatga tagggatgac attagatgtg ttaaaagtgt        780
taacaaccaa agctactacc acaatcttgt gctacaagac aaattacaag aattcaggaa        840
acagtaccct caagctgtca tactttatgc tgattactat gatgcctacc gcactgtcat        900
gaagaatcca agcaaatacg gattcaaaga gaccttcaac gtttgctgtg gatcaggaga        960
accaccttat aacttcactg tgtttgccac atgtggcaca cctaatgcca ctgtgtgttc       1020
aagcccttct cagtacatca attgggatgg tgttcatctc acggaggcca tgtacaaagt       1080
aatttctagt atgttttttgc aaggaaattt cacccaacct ccgtttaatt ttttgttgga       1140 aaaaaggag agggtggggt gaatggttag tatttgggat ttgcttgtcc ctatgacttt        1200
aatgcatcag ctaatgtaac tataagtgag ggaatcaggt cttacctgtt ttgctacaac       1260
ttgtgtcctc tgcacatcat atatgatgag aagttctaag gaatatgttg tatttgtatt       1320
agtatctgcc aaggctgtct taaactcggt attagctagt gcttactttg tttagattag       1380
ttgattttgg gttaataaag tgttttttct tttcttttta caaaaaaaaa aaaaaaaa         1439
```

<210> SEQ ID NO 26
<211> LENGTH: 380
<212> TYPE: PRT
<213> ORGANISM: Glycine max

<400> SEQUENCE: 26

```
Met Ala Ser Cys Val Ser Ser Met Ser Ser Thr Ile Leu Ile Leu Ile
  1               5                  10                  15

Ala Ile Cys Thr Leu Ser Ser Leu Leu Ser Ala Ala Ser Ala Ala Thr
             20                  25                  30

Glu Glu Gly Arg Thr Arg Pro Phe Lys Arg Val Tyr Ala Phe Gly Asp
         35                  40                  45

Ser Phe Thr Asp Thr Gly Asn Thr Lys Asn Ala Glu Gly Pro Ser Gly
     50                  55                  60

Phe Gly His Val Ser Asn Ser Pro Tyr Gly Thr Thr Phe Phe Asn His
 65                  70                  75                  80

Ser Thr Asn Arg Tyr Ser Asp Gly Arg Leu Val Ile Asp Phe Val Ala
                 85                  90                  95

Glu Ala Leu Ser Leu Pro Tyr Leu Pro Pro Tyr Arg His Ser Lys Gly
            100                 105                 110

Asn Asp Thr Phe Gly Val Asn Phe Ala Val Ala Gly Ser Thr Ala Ile
        115                 120                 125

Asn His Leu Phe Phe Val Lys His Asn Leu Ser Leu Asp Ile Thr Ala
    130                 135                 140

Gln Ser Ile Gln Thr Gln Met Ile Trp Phe Asn Arg Tyr Leu Glu Ser
145                 150                 155                 160

Gln Glu Cys Gln Glu Ser Lys Cys Asn Asp Phe Asp Asp Thr Leu Phe
                165                 170                 175

Trp Phe Gly Glu Ile Gly Val Asn Asp Tyr Ala Tyr Thr Leu Gly Ser
            180                 185                 190

Thr Val Ser Asp Glu Thr Ile Arg Lys Leu Ala Ile Ser Ser Val Ser
```

```
                195                 200                 205
Gly Ala Leu Gln Thr Leu Leu Glu Lys Gly Ala Lys Tyr Leu Val Val
    210                 215                 220

Gln Gly Met Pro Leu Thr Gly Cys Leu Thr Leu Ser Met Tyr Leu Ala
225                 230                 235                 240

Pro Pro Asp Asp Arg Asp Asp Ile Arg Cys Val Lys Ser Val Asn Asn
                245                 250                 255

Gln Ser Tyr Tyr His Asn Leu Val Leu Gln Asp Lys Leu Gln Glu Phe
                260                 265                 270

Arg Lys Gln Tyr Pro Gln Ala Val Ile Leu Tyr Ala Asp Tyr Tyr Asp
            275                 280                 285

Ala Tyr Arg Thr Val Met Lys Asn Pro Ser Lys Tyr Gly Phe Lys Glu
        290                 295                 300

Thr Phe Asn Val Cys Cys Gly Ser Gly Glu Pro Pro Tyr Asn Phe Thr
305                 310                 315                 320

Val Phe Ala Thr Cys Gly Thr Pro Asn Ala Thr Val Cys Ser Ser Pro
                325                 330                 335

Ser Gln Tyr Ile Asn Trp Asp Gly Val His Leu Thr Glu Ala Met Tyr
                340                 345                 350

Lys Val Ile Ser Ser Met Phe Leu Gln Gly Asn Phe Thr Gln Pro Pro
            355                 360                 365

Phe Asn Phe Leu Leu Glu Lys Lys Glu Arg Val Gly
    370                 375                 380

<210> SEQ ID NO 27
<211> LENGTH: 1256
<212> TYPE: DNA
<213> ORGANISM: Triticum aestivum

<400> SEQUENCE: 27
cttttctagt ccgaagacgc tagcgtctag ccttctttct ctaaaatggg gagtaccatt     60
tcattggccc tcctcttggt ctttgccgtc ctgctgctca acgctgatct agggtcgtgc    120
ggctgcttca agcgcatctt cgcattcggc gactccatca tcgacacggg caacttccac    180
ccaggttcga tgtggagccc cccttatgga gggacctact tccaccgtcc cacgggccgc    240
tgctcagacg ggcgtctcat tgtggacttc tacgcgcaag cgttggggct gccactgctc    300
ccaccgagcg ggcccgagga gaagacgggg cagttccgga ccggtgccaa cttcgccgtg    360
ttaggctcta ttgccctgag cccggactac tacagtaaaa ggtataactt cagtatgccg    420
cactggtgcc tcgactggga gctcggttcc ttcaaggcag tgctcgcacg gatagctcct    480
ggaaaagctg caaccaaacg tctcctcagc gagtccctca tcatctttgg cgagatcggt    540
ggcaacgact acaacttctg gttctacgat cgccagcgca ccgtgacac gccctataag    600 tacatgcccg acatcatcgc ccgcataggc tccggcgtcc aggaggtgat caacctcggt    660
gccaagacga tccttgttcc tggaaacttc cccatcgggt gtgtcccgat ttacctgagt    720
gggcacaaga ctaacaagtc tgccgactat gaccaattcg gctgcctcaa gtggtacaat    780
acgttctccc agaagcacaa ccaaatgttg aggcaggagg tcggccggct caggtctcgc    840
aaccctggcg tgaaggtcat ctacgccgac tactatggcg ccgccatgga gttttcagg    900 aaccctaaga ggcatggcat cgacgacccc ctggtggcgt gttgtggtgg caacggcccc    960
tacggcaccg gcgtgggtg cgatcagaac gcaaaggttt gccgtgaccc gtccaggttc   1020
gccaactggg accaggttca catgacggag aaggcataca gtgtcatcgc caatgggtg   1080
```

```
ctcaacggcc cgtatgcgga cattccgttg ctccacgctt gctaggagaa tttcctttcg    1140
agacttgaag aaatgttgct gcaaccaaga tctgttatgc gctagctttt ggaattttta    1200
atcttgtatc accatctcaa ttggtcatga atgaaatggt tggatctgtt gctaaa        1256
```

<210> SEQ ID NO 28
<211> LENGTH: 359
<212> TYPE: PRT
<213> ORGANISM: Triticum aestivum

<400> SEQUENCE: 28

```
Met Gly Ser Thr Ile Ser Leu Ala Leu Leu Val Phe Ala Val Leu
 1               5                  10                  15

Leu Leu Asn Ala Asp Leu Gly Ser Cys Gly Cys Phe Lys Arg Ile Phe
                 20                  25                  30

Ala Phe Gly Asp Ser Ile Ile Asp Thr Gly Asn Phe His Pro Gly Ser
             35                  40                  45

Met Trp Ser Pro Pro Tyr Gly Thr Tyr Phe His Arg Pro Thr Gly
         50                  55                  60

Arg Cys Ser Asp Gly Arg Leu Ile Val Asp Phe Tyr Ala Gln Ala Leu
 65                  70                  75                  80

Gly Leu Pro Leu Leu Pro Pro Ser Gly Pro Glu Glu Lys Thr Gly Gln
                 85                  90                  95

Phe Arg Thr Gly Ala Asn Phe Ala Val Leu Gly Ser Ile Ala Leu Ser
            100                 105                 110

Pro Asp Tyr Tyr Ser Lys Arg Tyr Asn Phe Ser Met Pro His Trp Cys
            115                 120                 125

Leu Asp Trp Glu Leu Gly Ser Phe Lys Ala Val Leu Ala Arg Ile Ala
130                 135                 140

Pro Gly Lys Ala Ala Thr Lys Arg Leu Leu Ser Glu Ser Leu Ile Ile
145                 150                 155                 160

Phe Gly Glu Ile Gly Gly Asn Asp Tyr Asn Phe Trp Phe Tyr Asp Arg
                165                 170                 175

Gln Arg Ser Arg Asp Thr Pro Tyr Lys Tyr Met Pro Asp Ile Ile Ala
            180                 185                 190

Arg Ile Gly Ser Gly Val Gln Glu Val Ile Asn Leu Gly Ala Lys Thr
        195                 200                 205

Ile Leu Val Pro Gly Asn Phe Pro Ile Gly Cys Val Pro Ile Tyr Leu
210                 215                 220

Ser Gly His Lys Thr Asn Lys Ser Ala Asp Tyr Asp Gln Phe Gly Cys
225                 230                 235                 240

Leu Lys Trp Tyr Asn Thr Phe Ser Gln Lys His Asn Gln Met Leu Arg
                245                 250                 255

Gln Glu Val Gly Arg Leu Arg Ser Arg Asn Pro Gly Val Lys Val Ile
            260                 265                 270

Tyr Ala Asp Tyr Tyr Gly Ala Ala Met Glu Phe Phe Arg Asn Pro Lys
        275                 280                 285

Arg His Gly Ile Asp Asp Pro Leu Val Ala Cys Cys Gly Gly Asn Gly
    290                 295                 300

Pro Tyr Gly Thr Gly Arg Gly Cys Asp Gln Asn Ala Lys Val Cys Arg
305                 310                 315                 320

Asp Pro Ser Arg Phe Ala Asn Trp Asp Gln Val His Met Thr Glu Lys
                325                 330                 335

Ala Tyr Ser Val Ile Ala Asn Gly Val Leu Asn Gly Pro Tyr Ala Asp
            340                 345                 350
```

Ile Pro Leu Leu His Ala Cys
        355

<210> SEQ ID NO 29
<211> LENGTH: 1472
<212> TYPE: DNA
<213> ORGANISM: Triticum aestivum

<400> SEQUENCE: 29

| | | | | |
|---|---|---|---|---|
| gcacgagccg cagcacatgc gcgtcgcccg ccgacaccca cacccacagc agcggcagcg | | | | 60 |
| gcaatggagc atcggggcct gcttctcgtc ctcgtcgcgg cggcgtgcct ctcgggcggc | | | | 120 |
| gcccacgcca ggcacgccaa gaagtcgtac ggggccgtct tcagcttcgg ggattcgctc | | | | 180 |
| tccgacgccg gcaacctcat cgtcgacggc atccccaagt cgctcaccac cgcgcggtcg | | | | 240 |
| ccctacggca tgaccttctt cggccgcccc accggccgct gctccaacgg ccgcgtcgtc | | | | 300 |
| gtcgacttcc tcgccgagca cttcgggctg cccctgccgc cggcgtcgca ggcgcatggc | | | | 360 |
| aaggacttca gaaggggggc caacttcgcc atcacgggcg ccacggcgct ggagtactcc | | | | 420 |
| ttcttcaagg cccacggcat cgaccagcgc atctggaaca ccggctccat taacacccag | | | | 480 |
| atcggctggc tccagaagat gaagccgtcg ctctgcaaat cggagaaaga gtgcagggac | | | | 540 |
| tacttcagca agtccctgtt cgtggtggga gagttcgggg ggaacgacta caacgctcct | | | | 600 |
| ctcttctccg gcgtcgcctt ctccgaggtg aagacctacg tgccgctggt cgccaaggcc | | | | 660 |
| atcgccaacg gcgtcgagaa attgatcgag cttggcgcga cggacctgtt ggtgcctgga | | | | 720 |
| attcttccga tcgggtgctt cccgttgtac ctgactctct acaacagcag caagaagtcc | | | | 780 |
| gactacaacg cgcgcacggg gtgcctccgg agatacaacc gtctggcctt ccaccacaac | | | | 840 |
| agggagctca gcagcagct cgacgcgctt cagaagaagt acccgaagac caaaatcatg | | | | 900 |
| tacggcgact acttcaaagc cgcaatgcag ttcgtcgtga gccccggaaa attcggcttc | | | | 960 |
| agcacggcat tgcaggcgtg ctgcggcgcc ggagggacgg gcgcctacaa cttcaacctg | | | | 1020 |
| aagaagaagt gcggcgaggc gggcgcgagc gtgtgctcca acccgtcggc gtacgtgagc | | | | 1080 |
| tgggacggca tccacatgac cgaggccgcc taccgcatgg tggccaacgg ttggctcaac | | | | 1140 |
| ggcccctacg cctctccccc gatcatgaag tgagagtcga catgactggc ccttagccgt | | | | 1200 |
| gtacctatgt atgtaacgtc gctgctgctg ctgctgctgc tgatgatgat gatgatgatg | | | | 1260 |
| gtgatggagg gatcggtgac atgcggagcg cttcaggcgc tggagatgtt aagttatgat | | | | 1320 |
| atgatgggag gttgtataaa ccgtgccggt atagatatgt tttccagctg aaaagctcta | | | | 1380 |
| gtagtagtac agatgtacgt accttgtatg acatgctacc tgattcttct tattcattta | | | | 1440 |
| ccaagacttg cataaaaaaa aaaaaaaaaa aa | | | | 1472 |

<210> SEQ ID NO 30
<211> LENGTH: 369
<212> TYPE: PRT
<213> ORGANISM: Triticum aestivum

<400> SEQUENCE: 30

Met Glu His Arg Gly Leu Leu Leu Val Leu Val Ala Ala Ala Cys Leu
 1               5                  10                  15

Ser Gly Gly Ala His Ala Arg His Ala Lys Lys Ser Tyr Gly Ala Val
            20                  25                  30

Phe Ser Phe Gly Asp Ser Leu Ser Asp Ala Gly Asn Leu Ile Val Asp
        35                  40                  45

```
Gly Ile Pro Lys Ser Leu Thr Thr Ala Arg Ser Pro Tyr Gly Met Thr
 50                  55                  60
Phe Phe Gly Arg Pro Thr Gly Arg Cys Ser Asn Gly Arg Val Val Val
 65                  70                  75                  80
Asp Phe Leu Ala Glu His Phe Gly Leu Pro Leu Pro Ala Ser Gln
                 85                  90                  95
Ala His Gly Lys Asp Phe Lys Lys Gly Ala Asn Phe Ala Ile Thr Gly
                100                 105                 110
Ala Thr Ala Leu Glu Tyr Ser Phe Phe Lys Ala His Gly Ile Asp Gln
                115                 120                 125
Arg Ile Trp Asn Thr Gly Ser Ile Asn Thr Gln Ile Gly Trp Leu Gln
130                 135                 140
Lys Met Lys Pro Ser Leu Cys Lys Ser Glu Lys Glu Cys Arg Asp Tyr
145                 150                 155                 160
Phe Ser Lys Ser Leu Phe Val Val Gly Glu Phe Gly Gly Asn Asp Tyr
                165                 170                 175
Asn Ala Pro Leu Phe Ser Gly Val Ala Phe Ser Glu Val Lys Thr Tyr
                180                 185                 190
Val Pro Leu Val Ala Lys Ala Ile Ala Asn Gly Val Glu Lys Leu Ile
                195                 200                 205
Glu Leu Gly Ala Thr Asp Leu Leu Val Pro Gly Ile Leu Pro Ile Gly
                210                 215                 220
Cys Phe Pro Leu Tyr Leu Thr Leu Tyr Asn Ser Ser Lys Lys Ser Asp
225                 230                 235                 240
Tyr Asn Ala Arg Thr Gly Cys Leu Arg Arg Tyr Asn Arg Leu Ala Phe
                245                 250                 255
His His Asn Arg Glu Leu Lys Gln Gln Leu Asp Ala Leu Gln Lys Lys
                260                 265                 270
Tyr Pro Lys Thr Lys Ile Met Tyr Gly Asp Tyr Phe Lys Ala Ala Met
                275                 280                 285
Gln Phe Val Val Ser Pro Gly Lys Phe Gly Phe Ser Thr Ala Leu Gln
                290                 295                 300
Ala Cys Cys Gly Ala Gly Gly Thr Gly Ala Tyr Asn Phe Asn Leu Lys
305                 310                 315                 320
Lys Lys Cys Gly Glu Ala Gly Ala Ser Val Cys Ser Asn Pro Ser Ala
                325                 330                 335
Tyr Val Ser Trp Asp Gly Ile His Met Thr Glu Ala Ala Tyr Arg Met
                340                 345                 350
Val Ala Asn Gly Trp Leu Asn Gly Pro Tyr Ala Ser Pro Pro Ile Met
                355                 360                 365
Lys
369
```

<210> SEQ ID NO 31
<211> LENGTH: 1226
<212> TYPE: DNA
<213> ORGANISM: Triticum aestivum

<400> SEQUENCE: 31

| | | | | |
|---|---|---|---|---|
| gcacgagcat | cctcttcctc | ttgagcgtct | ccctctgcgg | gacgtcgtgg | cagagctacg | 60 |
| atgcgatata | caacttcggc | gactccatct | ccgacaccgg | caacctctgc | acgggcggct | 120 |
| gcccgtcgtg | gctcaccatg | ggccagccgc | cgtacgggac | cagctacttc | ggccgcccga | 180 |
| caggacgctg | ctccgacggc | cgcgtcgtcg | tcgacttcct | cgctcagttc | ttccgtctgc | 240 |

```
cacttcttcc gccgtccaag tccaagacga acggcaccga cttcaggaaa ggcgccaaca    300
tggccatcat cggcgccacc gccatgaacc tggacttctt ccagtctcac ggcctgggca    360
gcagcatctg gaacaacggg cctctggaca cgcaaatcca gtggttcctg cagctcatgc    420
cttccatctg cggcggcgcc ggcgattgca ggagccacct gagcaagtcc ctgttcatct    480
tgggcgagtt cggggggcaac gactacaacg cggcgatctt cggcggcaag agcctggacg    540
aggtctacac ctacgtgcca cacatcatca acaaggtcac aagcggcgta gagacgctga    600
tcgggctggg cgcggtggac gtggtggtgc cgggcgtgct gccgatcggg tgcttcccgc    660
tctacctgac cctgtacggg agctccaacc agagcgacta cgatgggac ggctgcctca    720 ggcgcttcaa cgacctgtcc ggctaccaca ccggctgct caggcagggg atcggcaggc    780
tccggagcaa gtacgccggc gtcaggctca tgtacggcga cttctacacc caggtcgccg    840
agatggtccg ctctccccgg agcttcggac tggattacgg cctgactgtt tgttgcggcg    900
cgagcggcca agggtcatac aactacaata taaggcgag gtgtggcatg tccggctcaa    960
gcgcctgcaa ggaccctcag aactatttga actgggacgg catccgcttg actgagcatg   1020
cctaccgttc gatcgcgtat gggtggctca cagggcccta ctgtgtgccc gctattcttc   1080
attgagctac cgatggctac acatattggc taacagtaat gtgcactgta atgaaccaat   1140
aattcaaggg gatgctgccg atcaatgatg tttctgatgg agacccaagt ttgatataaa   1200
aaaaaaaaaa aaaaaaaaaa aaaaaa                                        1226

<210> SEQ ID NO 32
<211> LENGTH: 360
<212> TYPE: PRT
<213> ORGANISM: Triticum aestivum

<400> SEQUENCE: 32

Thr Ser Ile Leu Phe Leu Leu Ser Val Ser Leu Cys Gly Thr Ser Trp
 1               5                  10                  15

Gln Ser Tyr Asp Ala Ile Tyr Asn Phe Gly Asp Ser Ile Ser Asp Thr
            20                  25                  30

Gly Asn Leu Cys Thr Gly Gly Cys Pro Ser Trp Leu Thr Met Gly Gln
        35                  40                  45

Pro Pro Tyr Gly Thr Ser Tyr Phe Gly Arg Pro Thr Gly Arg Cys Ser
    50                  55                  60

Asp Gly Arg Val Val Asp Phe Leu Ala Gln Phe Phe Arg Leu Pro
65                  70                  75                  80

Leu Leu Pro Pro Ser Lys Ser Lys Thr Asn Gly Thr Asp Phe Arg Lys
                85                  90                  95

Gly Ala Asn Met Ala Ile Ile Gly Ala Thr Ala Met Asn Leu Asp Phe
            100                 105                 110

Phe Gln Ser His Gly Leu Gly Ser Ser Ile Trp Asn Asn Gly Pro Leu
        115                 120                 125

Asp Thr Gln Ile Gln Trp Phe Leu Gln Leu Met Pro Ser Ile Cys Gly
    130                 135                 140

Gly Ala Gly Asp Cys Arg Ser His Leu Ser Lys Ser Leu Phe Ile Leu
145                 150                 155                 160

Gly Glu Phe Gly Gly Asn Asp Tyr Asn Ala Ala Ile Phe Gly Gly Lys
                165                 170                 175

Ser Leu Asp Glu Val Tyr Thr Tyr Val Pro His Ile Ile Asn Lys Val
            180                 185                 190

Thr Ser Gly Val Glu Thr Leu Ile Gly Leu Gly Ala Val Asp Val Val
```

```
                    195                 200                 205
Val Pro Gly Val Leu Pro Ile Gly Cys Phe Pro Leu Tyr Leu Thr Leu
    210                 215                 220

Tyr Gly Ser Ser Asn Gln Ser Asp Tyr Asp Gly Asp Gly Cys Leu Arg
225                 230                 235                 240

Arg Phe Asn Asp Leu Ser Gly Tyr His Asn Arg Leu Leu Arg Gln Gly
                245                 250                 255

Ile Gly Arg Leu Arg Ser Lys Tyr Ala Gly Val Arg Leu Met Tyr Gly
            260                 265                 270

Asp Phe Tyr Thr Gln Val Ala Glu Met Val Arg Ser Pro Arg Ser Phe
        275                 280                 285

Gly Leu Asp Tyr Gly Leu Thr Val Cys Cys Gly Ala Ser Gly Gln Gly
    290                 295                 300

Ser Tyr Asn Tyr Asn Asn Lys Ala Arg Cys Gly Met Ser Gly Ser Ser
305                 310                 315                 320

Ala Cys Lys Asp Pro Gln Asn Tyr Leu Asn Trp Asp Gly Ile Arg Leu
                325                 330                 335

Thr Glu His Ala Tyr Arg Ser Ile Ala Tyr Gly Trp Leu Thr Gly Pro
            340                 345                 350

Tyr Cys Val Pro Ala Ile Leu His
        355                 360

<210> SEQ ID NO 33
<211> LENGTH: 1342
<212> TYPE: DNA
<213> ORGANISM: Triticum aestivum

<400> SEQUENCE: 33
gcacgaggtc cgtgggtcga gctagccagc tagtgagtga gtgtgtgtgt gcgcgccact    60
gctttgcggc gctgcggctc tcgcgcggtt ccatggcggt ctcccggctc tccgtgctcg   120
tcgccgcgct ggcctgctgc tgcctcgcgc ggctcgccca atgcggcggc gggggcggcg   180
ggcagaacta cacctccatg ttcagcttcg gcgactccct gaccgacacc ggcaacctgc   240
tcgtgtccag cccgctctcc ttcaacatcg tcggccgctt ccccctacggc atgacctact   300 tccaccgccc cacgggccgc tgctccgacg gccgcctcgt cgtcgacttc ctcgcgcaag   360
cgttcgggct gccgctgctg cagccgtacc tgtcgcgcgg ggaggacgtc cggcagggcg   420
tcaacttcgc cgtgggcggc gccacggcca tggatccgcc cttcttcgag gggatcgggg   480
cgtcggacaa gctctggacc aacctgtcgc tcagcgtcca gctcgactgg ttcgacaagc   540
tcaagccttc actctgcggc tcacccaaaa gttgcaagaa gtatttcagc cggtcgctct   600
tcctcgtggg ggagatcggg gggaacgact acaactacgc cttcttcaag ggcaagaccc   660
tggacgacgc caagtcctac gtccccaccg tctcctccgc catcatcgac gcaaccgaga   720
ggctgatcaa ggcaggcgcg atgcacctgg tggtgccggg gaacctgccg atgggtgct   780 cgtcggcgta cctgacgctg caccccggca ggagcaggag cgactacgac gccgtcgggt   840
gcctgaggac gtacaacgac ttcgcgcagc gccacaacgc catggtccag cagaagctgc   900
aggtgctccg gctcaagtac cccaaggctc ggatcatgta cgccgactac tacgcgcgg   960 ccatgtcctt cgccaagaac cccaagcagt tcgggttcaa gcaggggccg ctgaagacgt  1020
gctgcggcgg cggggggccg tacaacttca ccccaaggc gagctgcggc gtgcgggggt  1080
ccagcgtgtg cgccgacccg tcggcgtacg ccaactggga cggcgtccac ctgacggagg  1140
ccgcctacca cgccatcgcc gacagcatcc tccacggccc ctacaccagc ccaggctgc  1200
```

```
tctgaccctc agcctccttg cttctagcgt gtgtgcttgc ttgttaagct ccggtagttt    1260
tcgtgactga tctgtgtaat ggctatgcta tgggtgacca actggacaga agctaaaaaa    1320
aaaaaaaaaa gagagaacta gt                                              1342
```

<210> SEQ ID NO 34
<211> LENGTH: 370
<212> TYPE: PRT
<213> ORGANISM: Triticum aestivum

<400> SEQUENCE: 34

```
Met Ala Val Ser Arg Leu Ser Val Leu Val Ala Ala Leu Ala Cys Cys
  1               5                  10                  15

Cys Leu Ala Arg Leu Ala Gln Cys Gly Gly Gly Gly Gly Gly Gln Asn
             20                  25                  30

Tyr Thr Ser Met Phe Ser Phe Gly Asp Ser Leu Thr Asp Thr Gly Asn
         35                  40                  45

Leu Leu Val Ser Ser Pro Leu Ser Phe Asn Ile Val Gly Arg Phe Pro
 50                  55                  60

Tyr Gly Met Thr Tyr Phe His Arg Pro Thr Gly Arg Cys Ser Asp Gly
 65                  70                  75                  80

Arg Leu Val Val Asp Phe Leu Ala Gln Ala Phe Gly Leu Pro Leu Leu
                 85                  90                  95

Gln Pro Tyr Leu Ser Arg Gly Glu Asp Val Arg Gln Gly Val Asn Phe
            100                 105                 110

Ala Val Gly Gly Ala Thr Ala Met Asp Pro Pro Phe Phe Glu Gly Ile
        115                 120                 125

Gly Ala Ser Asp Lys Leu Trp Thr Asn Leu Ser Leu Ser Val Gln Leu
    130                 135                 140

Asp Trp Phe Asp Lys Leu Lys Pro Ser Leu Cys Gly Ser Pro Lys Ser
145                 150                 155                 160

Cys Lys Lys Tyr Phe Ser Arg Ser Leu Phe Leu Val Gly Glu Ile Gly
                165                 170                 175

Gly Asn Asp Tyr Asn Tyr Ala Phe Phe Lys Gly Lys Thr Leu Asp Asp
            180                 185                 190

Ala Lys Ser Tyr Val Pro Thr Val Ser Ser Ala Ile Ile Asp Ala Thr
        195                 200                 205

Glu Arg Leu Ile Lys Ala Gly Ala Met His Leu Val Val Pro Gly Asn
    210                 215                 220

Leu Pro Met Gly Cys Ser Ser Ala Tyr Leu Thr Leu His Pro Gly Arg
225                 230                 235                 240

Ser Arg Ser Asp Tyr Asp Ala Val Gly Cys Leu Arg Thr Tyr Asn Asp
                245                 250                 255

Phe Ala Gln Arg His Asn Ala Met Val Gln Gln Lys Leu Gln Val Leu
            260                 265                 270

Arg Leu Lys Tyr Pro Lys Ala Arg Ile Met Tyr Ala Asp Tyr Tyr Gly
        275                 280                 285

Ala Ala Met Ser Phe Ala Lys Asn Pro Lys Gln Phe Gly Phe Lys Gln
    290                 295                 300

Gly Pro Leu Lys Thr Cys Cys Gly Gly Gly Pro Tyr Asn Phe Asn
305                 310                 315                 320

Pro Lys Ala Ser Cys Gly Val Arg Gly Ser Ser Val Cys Ala Asp Pro
                325                 330                 335

Ser Ala Tyr Ala Asn Trp Asp Gly Val His Leu Thr Glu Ala Ala Tyr
```

340                 345                 350
His Ala Ile Ala Asp Ser Ile Leu His Gly Pro Tyr Thr Ser Pro Arg
                355                 360                 365
Leu Leu
    370

<210> SEQ ID NO 35
<211> LENGTH: 1334
<212> TYPE: DNA
<213> ORGANISM: Triticum aestivum

<400> SEQUENCE: 35

| | | | | | |
|---|---|---|---|---|---|
| tcggcactcc | cactctaaga | gctccgagcc | agccaacaat | ggcgtcctct | ccgctgctcg | 60 |
| tggcgcttgt | gatggtctcg | gcgtgcttcc | tggccgtgtc | cggccagaag | ttcaacgcca | 120 |
| tctacagctt | cggcgactcc | atgtcggaca | ccggcaacct | ctgcgtcaac | gggccccccg | 180 |
| ccggcctcac | cctcacccag | ccccctacg | gcgagacctt | ctttggccgt | gccacctgcc | 240 |
| gctgctccga | cggccgcctc | gtcgtcgact | tcctcgccga | gaagttcggg | ctgccgctgc | 300 |
| tgaagccgtc | gaagcagggc | ggcgcggact | tcaagcaggg | cgccaacatg | gccatcatcg | 360 |
| gcgccaccgc | catgggctcc | agcttcttcc | agtcgctcgg | cgtcggcgac | aagatctgga | 420 |
| acaacgggcc | cctcgacacc | cagatccagt | ggttccagaa | cctcctcccc | tccgtctgcg | 480 |
| gctcatcgtg | caagacgtac | ctgtccaagt | ccctgttcgt | gctgggcgag | ctgggcggga | 540 |
| acgactacaa | cgcgcagctc | ttcggcggct | acacgccgga | gcaggcggcc | gggcagagcc | 600 |
| ccaccatcgt | ggacgccatt | ggcgccggcg | ccgagaagct | catcgggctg | gcgccatgt | 660 |
| acgtcgtcat | ccccggggtg | ctccccgtcg | gctgcttccc | catctacctc | acgctctacc | 720 |
| agacctccaa | cgccggcgac | tacgaccagt | acggctgcct | gaagcggttc | aacgcgctgt | 780 |
| cggcccgcca | caactcgctg | ctccagagca | aggtgaccag | cctgcaggc | aagtaccct | 840 |
| acgccaagat | catgtacgcc | gacttctact | cccacgtctt | cgacatggtc | aagagccccg | 900 |
| ctagctacgg | gttcagcacg | aacctgaggg | cgtgctgcgg | cgcgggcggc | ggcaagtaca | 960 |
| actaccagaa | cggggctagg | tgcggcatgt | ccggcgcgtc | ggcgtgcggc | aacccatcgt | 1020 |
| cgtcgctgag | ctgggacggg | atccacctga | cggaggcggc | ctacaagaag | atcgccgacg | 1080 |
| gctgggtcaa | cgggccctac | tgccacccgg | ccatcctctc | ctagagcgag | cgaccgagct | 1140 |
| ccggctcgtc | gtttggttgc | ttcctttcat | tcctcgaagc | tggggaggga | atggattact | 1200 |
| attattttta | gcagaagaag | aagaagaaga | agaagatgtg | ttgcgagaat | aagcatcgat | 1260 |
| ttgattaatt | ctcgtgtaat | ttgcgcttgg | gctgaaagag | attcggcggt | tatttaaaaa | 1320 |
| aaaaaaaaaa | aaaa | | | | | 1334 |

<210> SEQ ID NO 36
<211> LENGTH: 361
<212> TYPE: PRT
<213> ORGANISM: Triticum aestivum

<400> SEQUENCE: 36

Met Ala Ser Ser Pro Leu Leu Val Ala Leu Val Met Val Ser Ala Cys
  1               5                  10                  15

Phe Leu Ala Val Ser Gly Gln Lys Phe Asn Ala Ile Tyr Ser Phe Gly
                 20                  25                  30

Asp Ser Met Ser Asp Thr Gly Asn Leu Cys Val Asn Gly Pro Pro Ala
             35                  40                  45

```
Gly Leu Thr Leu Thr Gln Pro Pro Tyr Gly Glu Thr Phe Phe Gly Arg
         50                  55                  60

Ala Thr Cys Arg Cys Ser Asp Gly Arg Leu Val Val Asp Phe Leu Ala
 65                  70                  75                  80

Glu Lys Phe Gly Leu Pro Leu Lys Pro Ser Lys Gln Gly Gly Ala
                 85                  90                  95

Asp Phe Lys Gln Gly Ala Asn Met Ala Ile Ile Gly Ala Thr Ala Met
            100                 105                 110

Gly Ser Ser Phe Phe Gln Ser Leu Gly Val Gly Asp Lys Ile Trp Asn
            115                 120                 125

Asn Gly Pro Leu Asp Thr Gln Ile Gln Trp Phe Gln Asn Leu Leu Pro
       130                 135                 140

Ser Val Cys Gly Ser Ser Cys Lys Thr Tyr Leu Ser Lys Ser Leu Phe
145                 150                 155                 160

Val Leu Gly Glu Leu Gly Gly Asn Asp Tyr Asn Ala Gln Leu Phe Gly
                165                 170                 175

Gly Tyr Thr Pro Glu Gln Ala Ala Gly Gln Ser Pro Thr Ile Val Asp
            180                 185                 190

Ala Ile Gly Ala Gly Ala Glu Lys Leu Ile Gly Leu Gly Ala Met Tyr
       195                 200                 205

Val Val Ile Pro Gly Val Leu Pro Val Gly Cys Phe Pro Ile Tyr Leu
       210                 215                 220

Thr Leu Tyr Gln Thr Ser Asn Ala Gly Asp Tyr Asp Gln Tyr Gly Cys
225                 230                 235                 240

Leu Lys Arg Phe Asn Ala Leu Ser Ala Arg His Asn Ser Leu Leu Gln
                245                 250                 255

Ser Lys Val Thr Ser Leu Gln Gly Lys Tyr Pro Tyr Ala Lys Ile Met
            260                 265                 270

Tyr Ala Asp Phe Tyr Ser His Val Phe Asp Met Val Lys Ser Pro Ala
       275                 280                 285

Ser Tyr Gly Phe Ser Thr Asn Leu Arg Ala Cys Cys Gly Ala Gly Gly
       290                 295                 300

Gly Lys Tyr Asn Tyr Gln Asn Gly Ala Arg Cys Gly Met Ser Gly Ala
305                 310                 315                 320

Ser Ala Cys Gly Asn Pro Ser Ser Ser Leu Ser Trp Asp Gly Ile His
                325                 330                 335

Leu Thr Glu Ala Ala Tyr Lys Lys Ile Ala Asp Gly Trp Val Asn Gly
            340                 345                 350

Pro Tyr Cys His Pro Ala Ile Leu Ser
            355                 360

<210> SEQ ID NO 37
<211> LENGTH: 1635
<212> TYPE: DNA
<213> ORGANISM: Triticum aestivum
<220> FEATURE:
<221> NAME/KEY: unsure
<222> LOCATION: (351)
<223> OTHER INFORMATION: n = a, c, g or t

<400> SEQUENCE: 37
ctgctccgct ctgctctctg ccccgcccgc cggctcatct ccgcgcgcag aggcagcgtc      60
gcagcgagca caccaccttc gacccctcct cctccccgta acctgccggc tcttcccgcc    120
gcctcgcttg cgagtgagac gatggcgagg ccgtcgtcgt cgccgatggc gacgaggctg    180
ccgctgttgc ttgtgctgct gtcgtcgctg gccctgcagg cggcggcgca gaagtacaat    240
```

-continued

```
gcggtgtaca gcttcggcga ctcgatcacg gacacgggca acctgtgcac caacggccgc    300
ccctcggcga tcaccttcac gcagccgccc tacggcgaga cctacttcgg nagccccacc    360
tgccgctgct ccgacggccg ggtcatcgtc gacttcctca gcaccaagta cggcctcccc    420
ttcctgcccc cctccaagtc cacctccgcc gacttcaaga agggcgccaa catggccatc    480
accggcgcca ccgccatgga cgccccttc ttccgctccc tcggcctctc ggacaagatc    540
tggaacaacg ggcccatcag cttccagctc cagtggttcc agaccatcac ctcctccgtc    600 tgcgcagca gctgcaagag ctacctggcc aactcgctct tcatcttcgg ggagttcggg    660
gggaacgact acaacgcgat gctgttcggc aactacaaca cggaccaggc gagcacgtac    720
gcgccgcaga tcgtggacac catcggcgcc ggcgtggaga gctggtcgc gatgggcgcg    780 gtggacgtgg tggtgccggg ggtgctcccc atcggctgct tccccatcta cctcaccatc    840
tacggcacct ccagcgccgc cgactacgac tccctcggct gcctcaagaa gttcaacgac    900
ctctccacgt accacaacag cctgctgcag gccaaggtgt cggcgctcca ggccaagtac    960
aagtcggcgc gcatcatgta cgccgacttc tacgccgggg tgtacgacat ggtccagagc   1020
cccagcaaat acgggttcag ctcggtgttc gaggcgtgct gcgggtcggg gggaggcaag   1080
tacaactacg ccaacagcgc gcggtgcggc atgtccggcg cctccgcctg cgccagcccg   1140
gcgtcgcacc tcagctggga cggcatccac ctcaccgagg ccgcctacaa gcagatcacc   1200
gacggctggc tcaacggcgc cttctgccac ccaggcatca cccactagcc agccactccc   1260
actggtcgat caatcagctc atgcatcgtc gtccatggat ccatcattaa tcaatcaatc   1320
aatcgattat tattattata ttattataat tatttgttca gtcgggttaa tttttaggaa   1380
acgtttctgg ggactggcta aggctgggtt cctggtctgg tccggtggca aaaatcggg    1440 gcgcgtgtgt ggtgatgaag aaagggggga aatgacggc aactctcgtg gaatagtact    1500
gcctgtgttg ctgtgaacct gtaacctccc cgcaaaaaaa aaaaaagaa cctgtaacct    1560 gataattgtt ttgttccacg gaaagtggt acagttgaat gaaaggaat gaataataa    1620 acacgataaa aaaaa                                                    1635
```

<210> SEQ ID NO 38
<211> LENGTH: 368
<212> TYPE: PRT
<213> ORGANISM: Triticum aestivum

<400> SEQUENCE: 38

```
Met Ala Arg Pro Ser Ser Pro Met Ala Thr Arg Leu Pro Leu Leu
  1               5                  10                  15

Leu Val Leu Leu Ser Ser Leu Ala Leu Gln Ala Ala Gln Lys Tyr
                 20                  25                  30

Asn Ala Val Tyr Ser Phe Gly Asp Ser Ile Thr Asp Thr Gly Asn Leu
         35                  40                  45

Cys Thr Asn Gly Arg Pro Ser Ala Ile Thr Phe Thr Gln Pro Pro Tyr
     50                  55                  60

Gly Glu Thr Tyr Phe Gly Ser Pro Thr Cys Arg Cys Ser Asp Gly Arg
 65                  70                  75                  80

Val Ile Val Asp Phe Leu Ser Thr Lys Tyr Gly Leu Pro Phe Leu Pro
                 85                  90                  95

Pro Ser Lys Ser Thr Ser Ala Asp Phe Lys Lys Gly Ala Asn Met Ala
            100                 105                 110

Ile Thr Gly Ala Thr Ala Met Asp Ala Pro Phe Phe Arg Ser Leu Gly
```

-continued

```
            115                 120                 125
Leu Ser Asp Lys Ile Trp Asn Asn Gly Pro Ile Ser Phe Gln Leu Gln
    130                 135                 140
Trp Phe Gln Thr Ile Thr Ser Ser Val Cys Gly Ser Ser Cys Lys Ser
145                 150                 155                 160
Tyr Leu Ala Asn Ser Leu Phe Ile Phe Gly Glu Phe Gly Gly Asn Asp
                165                 170                 175
Tyr Asn Ala Met Leu Phe Gly Asn Tyr Asn Thr Asp Gln Ala Ser Thr
            180                 185                 190
Tyr Ala Pro Gln Ile Val Asp Thr Ile Gly Ala Gly Val Glu Lys Leu
        195                 200                 205
Val Ala Met Gly Ala Val Asp Val Val Pro Gly Val Leu Pro Ile
    210                 215                 220
Gly Cys Phe Pro Ile Tyr Leu Thr Ile Tyr Gly Thr Ser Ser Ala Ala
225                 230                 235                 240
Asp Tyr Asp Ser Leu Gly Cys Leu Lys Lys Phe Asn Asp Leu Ser Thr
                245                 250                 255
Tyr His Asn Ser Leu Leu Gln Ala Lys Val Ser Ala Leu Gln Ala Lys
            260                 265                 270
Tyr Lys Ser Ala Arg Ile Met Tyr Ala Asp Phe Tyr Ala Gly Val Tyr
        275                 280                 285
Asp Met Val Gln Ser Pro Ser Lys Tyr Gly Phe Ser Val Phe Glu
    290                 295                 300
Ala Cys Cys Gly Ser Gly Gly Lys Tyr Asn Tyr Ala Asn Ser Ala
305                 310                 315                 320
Arg Cys Gly Met Ser Gly Ala Ser Ala Cys Ala Ser Pro Ala Ser His
                325                 330                 335
Leu Ser Trp Asp Gly Ile His Leu Thr Glu Ala Ala Tyr Lys Gln Ile
            340                 345                 350
Thr Asp Gly Trp Leu Asn Gly Ala Phe Cys His Pro Gly Ile Thr His
        355                 360                 365

<210> SEQ ID NO 39
<211> LENGTH: 394
<212> TYPE: PRT
<213> ORGANISM: Arabidopsis thaliana

<400> SEQUENCE: 39

Met Ala Ser Gln Asp Cys His Met Leu Leu Ser Phe Phe Ile Ser Thr
1               5                   10                  15
Phe Leu Ile Thr Val Val Thr Ser Gln Thr Arg Cys Arg Asn Phe Lys
            20                  25                  30
Ser Ile Ile Ser Phe Gly Asp Ser Ile Thr Asp Thr Gly Asn Leu Leu
        35                  40                  45
Gly Leu Ser Ser Pro Asn Asp Leu Pro Glu Ser Ala Phe Pro Pro Tyr
    50                  55                  60
Gly Glu Thr Phe Phe His His Pro Ser Gly Arg Phe Ser Asp Gly Arg
65                  70                  75                  80
Leu Ile Ile Asp Phe Ile Ala Glu Phe Leu Gly Ile Pro His Val Pro
                85                  90                  95
Pro Phe Tyr Gly Ser Lys Asn Gly Asn Phe Glu Lys Gly Val Asn Phe
            100                 105                 110
Ala Val Gly Gly Ala Thr Ala Leu Glu Cys Ser Val Leu Glu Glu Lys
        115                 120                 125
```

-continued

```
Gly Thr His Cys Ser Gln Ser Asn Ile Ser Leu Gly Asn Gln Leu Lys
        130                 135                 140

Ser Phe Lys Glu Ser Leu Pro Tyr Leu Cys Gly Ser Ser Pro Asp
145                 150                 155                 160

Cys Arg Asp Met Ile Glu Asn Ala Phe Ile Leu Ile Gly Glu Ile Gly
                165                 170                 175

Gly Asn Asp Tyr Asn Phe Pro Leu Phe Asp Arg Lys Asn Ile Glu Glu
            180                 185                 190

Val Lys Glu Leu Val Pro Leu Val Ile Thr Thr Ile Ser Ser Ala Ile
        195                 200                 205

Ser Glu Leu Val Asp Met Gly Ala Arg Thr Phe Leu Val Pro Gly Asn
    210                 215                 220

Phe Pro Leu Gly Cys Ser Val Ala Tyr Leu Thr Leu Tyr Glu Thr Pro
225                 230                 235                 240

Asn Lys Glu Glu Tyr Asn Pro Leu Thr Gly Cys Leu Thr Trp Leu Asn
                245                 250                 255

Asp Phe Ser Val Tyr His Asn Glu Gln Leu Gln Ala Glu Leu Lys Arg
            260                 265                 270

Leu Arg Asn Leu Tyr Pro His Val Asn Ile Ile Tyr Gly Asp Tyr Tyr
        275                 280                 285

Asn Thr Leu Leu Arg Leu Met Gln Glu Pro Ser Lys Phe Gly Leu Met
    290                 295                 300

Asp Arg Pro Leu Pro Ala Cys Cys Gly Leu Gly Gly Pro Tyr Asn Phe
305                 310                 315                 320

Thr Phe Ser Ile Lys Cys Gly Ser Lys Gly Val Glu Tyr Cys Ser Asp
                325                 330                 335

Pro Ser Lys Tyr Val Asn Trp Asp Gly Ile His Met Thr Glu Ala Ala
            340                 345                 350

Tyr Lys Trp Ile Ser Glu Gly Val Leu Thr Gly Pro Tyr Ala Ile Pro
        355                 360                 365

Pro Phe Asn Trp Ser Cys Leu Asp Ser Lys Ile Lys Asn Asn Glu Ser
370                 375                 380

Leu His Thr Gln Tyr Ser Leu Met Asn Ser
385                 390
```

<210> SEQ ID NO 40
<211> LENGTH: 384
<212> TYPE: PRT
<213> ORGANISM: Arabidopsis thaliana

<400> SEQUENCE: 40

```
Met Ala Ser Ser Leu Lys Lys Leu Ile Ser Ser Phe Leu Leu Val Leu
 1               5                  10                  15

Tyr Ser Thr Thr Ile Ile Val Ala Ser Ser Glu Ser Arg Cys Arg Arg
                20                  25                  30

Phe Lys Ser Ile Ile Ser Phe Gly Asp Ser Ile Ala Asp Thr Gly Asn
            35                  40                  45

Tyr Leu His Leu Ser Asp Val Asn His Leu Pro Gln Ser Ala Phe Leu
        50                  55                  60

Pro Tyr Gly Glu Ser Phe Phe His Pro Pro Ser Gly Arg Ala Ser Asn
65                  70                  75                  80

Gly Arg Leu Ile Ile Asp Phe Ile Ala Glu Phe Leu Gly Leu Pro Tyr
                85                  90                  95

Val Pro Pro Tyr Phe Gly Ser Gln Asn Val Ser Phe Glu Gln Gly Ile
            100                 105                 110
```

```
Asn Phe Ala Val Tyr Gly Ala Thr Ala Leu Asp Arg Ala Phe Leu Leu
            115                 120                 125
Gly Lys Gly Ile Glu Ser Asp Phe Thr Asn Val Ser Leu Ser Val Gln
        130                 135                 140
Leu Asp Thr Phe Lys Gln Ile Leu Pro Asn Leu Cys Ala Ser Ser Thr
145                 150                 155                 160
Arg Asp Cys Lys Glu Met Leu Gly Asp Ser Leu Ile Leu Met Gly Glu
                165                 170                 175
Ile Gly Gly Asn Asp Tyr Asn Tyr Pro Phe Phe Glu Gly Lys Ser Ile
            180                 185                 190
Asn Glu Ile Lys Glu Leu Val Pro Leu Ile Val Lys Ala Ile Ser Ser
        195                 200                 205
Ala Ile Val Asp Leu Ile Asp Leu Gly Gly Lys Thr Phe Leu Val Pro
    210                 215                 220
Gly Gly Phe Pro Thr Gly Cys Ser Ala Ala Tyr Leu Thr Leu Phe Gln
225                 230                 235                 240
Thr Val Ala Glu Lys Asp Gln Asp Pro Leu Thr Gly Cys Tyr Pro Leu
                245                 250                 255
Leu Asn Glu Phe Gly Glu His His Asn Glu Gln Leu Lys Thr Glu Leu
            260                 265                 270
Lys Arg Leu Gln Lys Phe Tyr Pro His Val Asn Ile Ile Tyr Ala Asp
        275                 280                 285
Tyr His Asn Ser Leu Tyr Arg Phe Tyr Gln Glu Pro Ala Lys Tyr Gly
    290                 295                 300
Phe Lys Asn Lys Pro Leu Ala Ala Cys Cys Gly Val Gly Gly Lys Tyr
305                 310                 315                 320
Asn Phe Thr Ile Gly Lys Glu Cys Gly Tyr Glu Gly Val Asn Tyr Cys
                325                 330                 335
Gln Asn Pro Ser Glu Tyr Val Asn Trp Asp Gly Tyr His Leu Thr Glu
            340                 345                 350
Ala Ala Tyr Gln Lys Met Thr Glu Gly Ile Leu Asn Gly Pro Tyr Ala
        355                 360                 365
Thr Pro Ala Phe Asp Trp Ser Cys Leu Gly Ser Gly Thr Val Asp Thr
    370                 375                 380

<210> SEQ ID NO 41
<211> LENGTH: 381
<212> TYPE: PRT
<213> ORGANISM: Arabidopsis thaliana

<400> SEQUENCE: 41

Met Ser Ser Ser Ile Ser Pro Leu Leu Thr Thr Ala Ile Ser Val Ala
  1               5                  10                  15
Ile Leu Leu Phe Ser Thr Ile Ser Thr Ala Ala Thr Ile Pro Asn Ile
             20                  25                  30
His Arg Pro Phe Asn Lys Ile Tyr Ala Phe Gly Asp Ser Phe Thr Asp
         35                  40                  45
Thr Gly Asn Ser Arg Ser Gly Glu Gly Pro Ala Gly Phe Gly His Leu
     50                  55                  60
Ser Ser Pro Pro Tyr Gly Met Thr Phe Phe Arg Arg Pro Thr Asn Arg
 65                  70                  75                  80
Tyr Ser Asp Gly Arg Leu Thr Ile Asp Phe Val Ala Glu Ser Met Asn
                 85                  90                  95
Leu Pro Phe Leu Pro Pro Tyr Leu Ser Leu Lys Thr Thr Asn Ala Asn
```

-continued

```
                    100                 105                 110
Gly Thr Ala Thr Asp Thr His Gly Val Asn Phe Ala Val Ser Gly Ser
            115                 120                 125

Thr Val Ile Lys His Ala Phe Phe Val Lys Asn Asn Leu Ser Leu Asp
        130                 135                 140

Met Thr Pro Gln Ser Ile Glu Thr Glu Leu Ala Trp Phe Glu Lys Tyr
145                 150                 155                 160

Leu Glu Thr Leu Gly Thr Asn Gln Lys Val Ser Leu Phe Lys Asp Ser
                165                 170                 175

Leu Phe Trp Ile Gly Glu Ile Gly Val Asn Asp Tyr Ala Tyr Thr Leu
            180                 185                 190

Gly Ser Thr Val Ser Ser Asp Thr Ile Arg Glu Leu Ser Ile Ser Thr
        195                 200                 205

Phe Thr Arg Phe Leu Glu Thr Leu Leu Asn Lys Gly Val Lys Tyr Met
        210                 215                 220

Leu Val Gln Gly His Pro Ala Thr Gly Cys Leu Thr Leu Ala Met Ser
225                 230                 235                 240

Leu Ala Ala Glu Asp Asp Arg Asp Ser Leu Gly Cys Val Gln Ser Ala
                245                 250                 255

Asn Asn Gln Ser Tyr Thr His Asn Leu Ala Leu Gln Ser Lys Leu Lys
                260                 265                 270

Gln Leu Arg Ile Lys Tyr Pro Ser Ala Thr Ile Val Tyr Ala Asp Tyr
            275                 280                 285

Trp Asn Ala Tyr Arg Ala Val Ile Lys His Pro Ser Lys Tyr Gly Ile
        290                 295                 300

Thr Glu Lys Phe Lys Ala Cys Cys Gly Ile Gly Glu Pro Tyr Asn Phe
305                 310                 315                 320

Gln Val Phe Gln Thr Cys Gly Thr Asp Ala Ala Thr Val Cys Lys Asp
                325                 330                 335

Pro Asn Gln Tyr Ile Asn Trp Asp Gly Val His Leu Thr Glu Ala Met
            340                 345                 350

Tyr Lys Val Met Ala Asp Met Phe Leu Asp Gly Thr Phe Thr Arg Pro
        355                 360                 365

Arg Phe Ser Asp Leu Leu Ile Lys Lys Leu Asn Tyr Leu
370                 375                 380
```